US010166196B2

(12) United States Patent
Yan et al.

(10) Patent No.: US 10,166,196 B2
(45) Date of Patent: Jan. 1, 2019

(54) VEGETARIAN MICROCAPSULES

(75) Inventors: Cuie Yan, Dartmouth (CA); Wei Zhang, Halifax (CA); Yulai Jin, Battle Creek, MI (US); Lesek Alexa Demont, Chester (CA); Colin James Barrow, Torquay (AU)

(73) Assignee: DSM NUTRITIONAL PRODUCTS AG, Kaiseraugst (CH)

( * ) Notice: Subject to any disclaimer, the term of this patent is extended or adjusted under 35 U.S.C. 154(b) by 889 days.

(21) Appl. No.: 12/522,826

(22) PCT Filed: Jan. 9, 2008

(86) PCT No.: PCT/US2008/000301
§ 371 (c)(1),
(2), (4) Date: Mar. 25, 2010

(87) PCT Pub. No.: WO2008/085997
PCT Pub. Date: Jul. 17, 2008

(65) Prior Publication Data
US 2011/0117180 A1    May 19, 2011

Related U.S. Application Data

(60) Provisional application No. 60/879,636, filed on Jan. 10, 2007, provisional application No. 60/879,759, filed on Jan. 10, 2007.

(51) Int. Cl.
| | |
|---|---|
| A61L 9/16 | (2006.01) |
| A61K 9/50 | (2006.01) |
| A61K 8/11 | (2006.01) |
| A61K 8/64 | (2006.01) |
| A61K 8/65 | (2006.01) |
| A61K 8/73 | (2006.01) |
| A61Q 19/00 | (2006.01) |
| A23P 10/30 | (2016.01) |
| A23L 33/115 | (2016.01) |
| A23L 33/12 | (2016.01) |

(52) U.S. Cl.
CPC .......... *A61K 9/5089* (2013.01); *A23L 33/115* (2016.08); *A23L 33/12* (2016.08); *A23P 10/30* (2016.08); *A61K 8/11* (2013.01); *A61K 8/64* (2013.01); *A61K 8/645* (2013.01); *A61K 8/65* (2013.01); *A61K 8/73* (2013.01); *A61K 8/733* (2013.01); *A61K 9/5036* (2013.01); *A61K 9/5052* (2013.01); *A61K 9/5057* (2013.01); *A61K 9/5073* (2013.01); *A61Q 19/00* (2013.01); *A61K 2800/412* (2013.01)

(58) Field of Classification Search
None
See application file for complete search history.

(56) References Cited

U.S. PATENT DOCUMENTS

| | | |
|---|---|---|
| 2,800,457 A | 7/1957 | Green et al. |
| 2,800,458 A | 7/1957 | Green |
| 3,041,289 A | 6/1962 | Katchen et al. |
| 3,179,600 A | 4/1965 | Brockett |
| 3,190,837 A | 6/1965 | Brynko |
| 3,526,682 A | 9/1970 | Timreck |
| 3,697,437 A | 10/1972 | Fogel et al. |
| 4,010,038 A | 3/1977 | Iwasaki et al. |
| 4,217,370 A | 8/1980 | Rawlings et al. |
| 4,219,439 A | 8/1980 | Miyake et al. |
| 4,222,891 A | 9/1980 | Okimoto et al. |
| 4,232,084 A | 11/1980 | Tate |
| 4,273,672 A | 6/1981 | Vassiliades |
| 4,442,051 A | 4/1984 | Rowe et al. |
| 4,485,172 A | 11/1984 | Gierhart |
| 4,670,247 A | 6/1987 | Scialpi |
| 4,695,466 A | 9/1987 | Morishita et al. |
| 4,744,933 A | 5/1988 | Rha et al. |
| 4,749,620 A | 6/1988 | Rha et al. |
| 4,808,408 A | 2/1989 | Baker et al. |
| 4,861,627 A | 8/1989 | Mathiowitz et al. |
| 4,867,986 A | 9/1989 | Desai et al. |
| 4,891,172 A | 1/1990 | Matsushita et al. |
| 4,895,725 A | 1/1990 | Kantor et al. |
| 4,923,855 A | 5/1990 | Jensen |
| 4,946,624 A | 8/1990 | Michael |
| 4,954,492 A | 9/1990 | Jensen |
| 4,963,367 A | 10/1990 | Ecanow |
| 5,013,569 A | 5/1991 | Rubin |
| 5,035,896 A | 7/1991 | Apfel et al. |
| 5,051,304 A | 9/1991 | David et al. |
| 5,059,622 A | 10/1991 | Sears |
| 5,130,061 A | 7/1992 | Cornieri et al. |

(Continued)

FOREIGN PATENT DOCUMENTS

| | | |
|---|---|---|
| CA | 2318539 A1 | 7/1999 |
| CA | 2447002 | 4/2003 |

(Continued)

OTHER PUBLICATIONS

KM Kim, CL Weller, MA Hanna, A Gennadios. "Heat Curing of Soy Protein Films at Selected Temperatures and Pressures." Lebensmittel-Wissenschaft und-Technologie, vol. 35, 2002, pp. 140-145.*

I Chourpa, V Ducel, J Richard, P Dubois, F Boury. "Conformational Modifications of Alpha-Gliadin and Globulin Proteins upon Complex Coacervates Formation with Gum Arabic as Studied by Raman Microspectroscopy." Biomacromolecules, vol. 7, 2006, 2616-2623, published on web Aug. 25, 2006.*

DJ Burgess. "17 Complex Coacervation: Microcapsule Formation." Macromolecular Complexes in Chemistry and Biology. Editors: Dubin/Bock/Davis/Schulz/Thies. Springer-Verlag, Berlin Heidelberg. 1994, pp. 285-300 included.*

(Continued)

*Primary Examiner* — Isaac Shomer
(74) *Attorney, Agent, or Firm* — Nixon & Vanderhye P.C.

(57) ABSTRACT

Disclosed are microcapsules with shells that are not animal by-products and methods for preparing and using such microcapsules.

12 Claims, No Drawings

(56) References Cited

U.S. PATENT DOCUMENTS

| | | |
|---|---|---|
| 5,156,956 A | 10/1992 | Motoki |
| 5,173,321 A * | 12/1992 | Hosogoe et al. ............ 426/573 |
| 5,194,615 A | 3/1993 | Jensen |
| 5,204,029 A | 4/1993 | Morgan et al. |
| 5,330,778 A | 7/1994 | Stark |
| 5,342,626 A | 8/1994 | Winston, Jr. et al. |
| 5,356,636 A | 10/1994 | Schneider |
| 5,378,413 A | 1/1995 | Mihm et al. |
| 5,428,014 A | 6/1995 | Labroo |
| 5,456,985 A | 10/1995 | Zaoulli et al. |
| 5,573,934 A | 11/1996 | Hubbell et al. |
| 5,603,952 A | 2/1997 | Soper |
| 5,603,961 A | 2/1997 | Suzuki et al. |
| 5,670,209 A | 9/1997 | Wyckoff |
| 5,700,397 A | 12/1997 | Maeda et al. |
| 5,759,599 A | 6/1998 | Wampler et al. |
| 5,766,637 A | 6/1998 | Shine et al. |
| 5,780,056 A | 7/1998 | Akamatsu et al. |
| 5,788,991 A | 8/1998 | Natske et al. |
| 5,827,531 A | 10/1998 | Morrison et al. |
| 5,855,826 A | 1/1999 | Lee et al. |
| 5,872,140 A | 2/1999 | Hesse et al. |
| 5,993,851 A | 11/1999 | Foldvari |
| 5,997,863 A | 12/1999 | Zimmermann |
| 6,019,998 A | 2/2000 | Nomoto et al. |
| 6,020,200 A | 2/2000 | Enevol |
| 6,039,901 A | 3/2000 | Soper |
| 6,063,820 A | 5/2000 | Cavazza |
| 6,103,378 A | 8/2000 | Yao et al. |
| 6,106,875 A | 8/2000 | Soper et al. |
| 6,221,401 B1 | 4/2001 | Zasadzinski et al. |
| 6,234,464 B1 | 5/2001 | Krumbholz et al. |
| 6,274,174 B1 | 8/2001 | Hom-ma et al. |
| 6,300,377 B1 | 10/2001 | Chopra |
| 6,325,951 B1 | 12/2001 | Soper et al. |
| 6,328,995 B1 | 12/2001 | Bewert |
| 6,365,176 B1 | 4/2002 | Bell et al. |
| 6,417,233 B1 | 7/2002 | Sears et al. |
| 6,441,050 B1 | 8/2002 | Chopra |
| 6,482,433 B1 | 11/2002 | DeRoos et al. |
| 6,500,463 B1 | 12/2002 | van Lengerich |
| 6,528,165 B2 | 3/2003 | Chandler |
| 6,534,091 B1 | 3/2003 | Garces et al. |
| 6,534,094 B2 | 3/2003 | Moyano et al. |
| 6,534,926 B1 | 3/2003 | Miller et al. |
| 6,544,926 B1 | 4/2003 | Bodmer et al. |
| 6,630,157 B1 | 10/2003 | Horrobin et al. |
| 6,652,891 B2 | 11/2003 | Selzer |
| 6,969,530 B1 | 11/2005 | Curtis et al. |
| 6,972,592 B2 | 12/2005 | Benware |
| 6,974,592 B2 | 12/2005 | Yan et al. |
| 7,727,692 B2 | 6/2010 | Yan |
| 2002/0031553 A1 | 3/2002 | Moyano et al. |
| 2003/0044380 A1 | 1/2003 | Zhu et al. |
| 2003/0078617 A1* | 4/2003 | Schwartz et al. ............ 606/230 |
| 2003/0133886 A1 | 7/2003 | Smith et al. |
| 2003/0193102 A1 | 10/2003 | Yan |
| 2004/0106591 A1 | 6/2004 | Pacioretti et al. |
| 2004/0234601 A1* | 11/2004 | Legrand et al. ............ 424/469 |
| 2005/0042341 A1* | 2/2005 | Thomas et al. ............ 426/321 |
| 2005/0067726 A1* | 3/2005 | Yan et al. ............ 264/4.1 |
| 2005/0249952 A1 | 11/2005 | Vasishtha et al. |
| 2007/0027028 A1 | 2/2007 | Pears et al. |
| 2007/0059340 A1 | 3/2007 | Bello et al. |
| 2007/0078071 A1 | 4/2007 | Lee |
| 2007/0141211 A1 | 6/2007 | Kolar et al. |
| 2007/0224216 A1 | 9/2007 | Teas |
| 2009/0274791 A1 | 11/2009 | Mattson |
| 2010/0055281 A1 | 3/2010 | Barrow |
| 2010/0173002 A1 | 7/2010 | Jin |

FOREIGN PATENT DOCUMENTS

| | | |
|---|---|---|
| DE | 1035319 | 7/1958 |
| EP | 0301777 | 2/1989 |
| EP | 0416575 | 3/1991 |
| EP | 0426428 | 5/1991 |
| EP | 0434760 | 1/1994 |
| EP | 0782833 | 7/1997 |
| EP | 0856355 | 8/1998 |
| EP | 1116516 | 7/2001 |
| EP | 0821881 | 9/2001 |
| EP | 0644771 | 8/2002 |
| EP | 1237423 | 9/2002 |
| EP | 0982038 | 1/2003 |
| EP | 0745670 | 6/2004 |
| EP | 1357977 B1 | 7/2004 |
| EP | 0897970 | 9/2004 |
| GB | 1198412 | 7/1970 |
| GB | 2091286 | 7/1982 |
| GB | 2115768 | 9/1983 |
| JP | 5394273 A | 8/1978 |
| JP | 5828234 | 2/1983 |
| JP | 58149645 | 9/1983 |
| JP | 61172807 | 8/1986 |
| JP | 1148338 | 6/1989 |
| JP | 02086743 | 3/1990 |
| JP | 5292899 | 11/1993 |
| JP | 2002/028473 | 1/2002 |
| JP | 2004/054702 | 7/2004 |
| JP | 2005/522313 | 7/2005 |
| JP | 2006/506410 | 2/2006 |
| WO | WO 91/06287 | 5/1991 |
| WO | WO 92/11083 | 7/1992 |
| WO | WO 97/13416 | 4/1997 |
| WO | WO 97/040701 | 11/1997 |
| WO | WO 2001/080656 | 11/2001 |
| WO | WO 2002/096408 | 12/2002 |
| WO | WO2003086104 A1 | 10/2003 |
| WO | WO 2003/105606 | 12/2003 |
| WO | WO 2003/106014 | 12/2003 |
| WO | WO 2004054702 A1 * | 7/2004 |
| WO | WO 2006091101 A2 * | 8/2006 ............ A23L 1/0524 |
| WO | WO2007054207 A1 | 5/2007 |
| WO | WO2007055815 A1 | 5/2007 |

OTHER PUBLICATIONS

Office Action for U.S. Appl. No. 11/988,320 dated Sep. 1, 2011.
Bohnet et al., Ullmann's Encyclopedia of Industrial Chemistry, vol. II, p. 668, right column (2003).
Examination report for Application No. 200780019734.2 dated May 6, 2011.
Examination report for Application No. MX/a/2008/012967 dated Apr. 27, 2011.
Examination report for Application No. 200780029069.5 dated Feb. 24, 2011.
Examination report for Application No. 07825594.0 dated Mar. 30, 2011.
Examination report for Application No. 200880007740.0 dated Mar. 23, 2011.
Examination report for Application No. 2003-583137 dated May 10, 2011.
Limmer, "Remington: The Science and Practice of Pharmacy," p. 332, left column (2000).
Notice of Allowance for U.S. Appl. No. 11/227,961 dated Jun. 14, 2011.
Reasons for Submission on behalf of Japan Capsular Products Inc. filed in Japanese Patent Application No. 2003-583137 on Nov. 26, 2010.
Response to Opposition for Application No. EP06020381.7 dated Jun. 29, 2011.
Examination Report for Application No. 565606 dated May 13, 2010.
Examination Report for Application No. 573327 dated Nov. 16, 2011.
Examination Report for Application No. 596403 dated Nov. 16, 2011.
Office Action for Application No. 200680032544.X dated Oct. 20, 2011.
Office Action for Application No. 200800269 dated Mar. 18, 2010.

(56) References Cited

OTHER PUBLICATIONS

Office Action for Application No. 07754635.6 dated Aug. 26, 2011.
Office Action for Application No. 08713076.1 dated Sep. 21, 2011.
Office Action for Application No. 2008-520263 dated Feb. 22, 2011.
Office Action for Application No. 7007996/2005 dated Nov. 4, 2011.
Office Action for Application No. MX/a/2008/000210 dated Oct. 20, 2011.
Office Action for U.S. Appl. No. 11/918,150 dated Nov. 16, 2011.
Office Action for U.S. Appl. No. 12/308,045 dated Sep. 9, 2011.
Appel et al., "Does supplementation of diet with 'fish oil' reduce blood pressure? A meta-analysis of controlled clinical trials," *Arch Intern Med.*, 153(12):1429-1438 (1993).
Barrow et al., "Stabilization of highly unsaturated fatty acids and delivery into foods," *Lipid Technology*, 9(5):108-111 (2007).
Beestman, "Microencapsulation of Solid Particles," Chemical Abstract, Abstracts of Papers, 220$^{th}$ ACS National Meeting, Washington, DC, United States, Aug. 20-24, 2000, AGRO-037. CODEN: 69FZC3 AN 2000:793223.
Boh et al., "Microcapsule Applications: Patent and Literature Analysis," *MML Series*, 6:85-156 (2003).
Borghi, "Omega-3 LC PUFAs, A new solution for pasteurized milk enrichment," *Wellness Foods Europe*, pp. 25-26 (May 2005).
Calon et al., "Docosahexaenoic acid protects from dentritic pathology in an Alzeheimer's Disease mouse model," *Neuron*, 43:633-645 (2004).
Choi et al., "Physicochemical and sensory characteristics of fish gelatin," *J. Food Sci. Food Chemistry and Toxicology*, 65:194-199 (2000).
Dyrberg et al., "In Omega-3 fatty acids: prevention and treatment of vascular disease," Kristensen et al., Eds. Bi. & Gi Publ., Verona-Springer-Verlag, London, pp. 217-226 (1995).
European Patent Office European Search Report for 06020381.7 dated Apr. 10, 2007.
Fong, "Microencapsulation by solvent and organic phase separation processes," *Controlled Release Systems: Fabrication Technology*, Hsieh Ed., CRC Press, New York, pp. 99-105 (1988).
GISSI-Prevenzione Investigators, "Dietary supplementation with Omega-3 polyunsaturated fatty acids and vitamin E after myocardial infarction: results of the GISSI-Prevenzione trial," *Lancet*, 354:447-455 (1999).
Goyer, "Toxic effects of metals," *Casarett and Doull's Toxicology*, Amdur et al., Eds., 4$^{th}$ ed., Pergamon Press, New York, pp. 638-639 (1991).
Harris, "Extending the cardiovascular benefits of Omega-3 fatty acids," *Curr. Atheroscler Rep.*, 7:375-380 (2005).
Haug et al., "Physical and rheological properties of fish gelatin compared to mammalian gelatin," *Food Hydrocolloids*, 18:203-213 (2004).
Holub, "Clinical Nutrition: 4 Omega-3 fatty acids in cardiovascular care," *CMAJ*, 166(5):608-615 (2002).
Ijichi et al., "Multi-Layered Gelatin Acacia Microcapsules by Complext Coacervation Method," *J. of Chem Eng. of Japan.*, 30(5):793-798 (1997).
International Search Report and Written Opinion for PCT/US08/000301 dated Apr. 30, 2008.
International Search Report and Written Opinion for PCT/US07/008138 dated May 9, 2008.
International Search Report and Written Opinion for PCT/IB07/03358 dated Apr. 25, 2008.
European Search Authority International Search Report for PCT/IB2006/001214 and Written Opinion dated Feb. 8, 2007.
International Search Report and Written Opinion for PCT/IB06/01526 dated Aug. 22, 2006.
Kage et al., "Microencapsulation of mono-dispersed droplets by complex coacervation and membrane thickness of generated capsules," Chemical Abstract No. Accession 615273 (2000).
Kas et al., "Microencapsulation using coacervatoin/phrase separation," *In Handbook of Pharmaceutical Controlled Release Technology*, Wise Ed., Marcel Dekker Inc., New York, pp. 301-328 (2000).

Kris-Etherton et al., "Fish consumption, fish oil, Omega-3 fatty acids and cardiovascular disease," *The American Heart Association Scientific Statement*, 106(21):2747-2757 (Nov. 2002).
Kondo et al., "Microencapsulation utilizing phase separation from an aqueous solution system," *Microcapsule Processing and Technology*, Marcel Dekker Inc., New York, pp. 70-95 (1979).
Leclercq et al., "Formation and characterization of microcapsules by complex coacervation with liquid or solid aroma cores," *Flavour Fragr. J.*, 24:17-24 (2009).
Magdassi et al., "Microencapsulation of Oil-in-Water Emulsions by Proteins," *Microencapsulation—Methods and Industrial Applications*, edited by Simon Benita, Marcel Dekker, Inc., New York, pp. 21-33 (1996).
Marcus et al., "The Vitamins," *Goodman and Gilman's The Pharmacological Basis of Therapeutics*, McGraw-Hill, Inc., New York, pp. 1524-1527 (1990).
Mori et al., "Purified eicosapentaenoic and docosapentaenoic acids have differential effects on serum lipids and lipoproteins, LDL particle size, glucose, and insulin in mildly hypelipidemic men," *Am. J. Clin. Nutr.*, 71:1085-1094 (2000).
Muskiet et al., "Is docosahexaenoic acid (DHA) essential? Lessons from DHA status regulation, our ancient diet, epidemiology and randomized controlled trials," *J. Nutr.*, 134(1):183-186 (2004).
O'Keefe et al., "Omega-3 acids: Time for clinical implementation?" *Am. J Cardiology*, 85:1239-1241 (20002).
Onuki et al., "In vivo effects of highly purified docosahexaenoic acid on rectal insulin absorption," *Int. J. Pharm.*, 198:147-156 (2000).
Ovide-Borodeaux et al., "Docosahexaenoic acid affects insulin-deficiency and insul resistant-induced alterations in cardiac mitochondria," *Am. J Physiool. Regul. Integr. Comp. Physiol.*, 286:R519-R527 (2003).
Radack et al., "The effects of low doses of Omega-3 fatty acid supplementation on blood pressure in hypertensive subjects: a randomized controlled trial," *Arch. Intern. Med.*, 151:1173-1180 (1991).
Recommended Daily Allowances, Ninth Revised Edition, The Natural Academy of Sciences, p. 160 (1980).
Soper, "Utilization of coacervated flavors," *Encapsulation and Controlled Release of Food Ingredients*, Risch and Reineccius Ed., ACS Symposium Series 590, Washington, D.C., pp. 104-112 (1995).
Sparks, "Microencapsulation," *Kirk-Othmer, Encyclopedia of Chemical Technology*, vol. 15, 3$^{rd}$ Ed., John Wiley & Sons Inc., New York, pp. 470-793 (1981).
Sugano et al., "Balanced intake of polyunsaturated fatty acids for health benefits," *J. Oleo. Sci.*, 50(5):305-311 (2001).
Thimma et al., "Study of complex coacervation of gelatin with sodium carboxymethyl guar gum: Microencapsulation of close oil and sulphamethoxazole," *J. Microencapsulation*, 20(2):203-210 (2003).
Webb, "Alternative sources of Omega-3 fatty acids," *Natural Foods Merchandiser*, XXVI(8):40-44 (2005).
Whorton et al., "Evaluation of the mechanisms associated with the release of encapsulated flavor form maltodextrin matrices," *Encapsulation and Controlled Release of Food Ingredients*, Risch and Reineccius Ed., ACS Symposium Series 590, Washington, D.C., pp. 143-160 (1995).
Yoshida et al., "Manufacture of microcapsules from complex coacervation processes," *Chemical Abstract*, Accession No. 140735 (1990).
Examination Report for Application No. CL 2008-63 dated May 15, 2012.
Examination Report for Application No. JP 2009-545586 dated Sep. 19, 2012.
Examination Report for Application No. NZ 600903 dated Jul. 3, 2012.
Examination Report for Application No. JP 2003-583137 dated Aug. 24, 2012.
Examination Report for Application No. JP 2010-190957 dated Oct. 16, 2012.
Office Action for U.S. Appl. No. 12/768,152 dated Sep. 12, 2012.
Office Action for U.S. Appl. No. US 13/009,418 dated Sep. 5, 2012.
Examination Report for Application No. AU 2007282922 dated Mar. 2, 2012.

(56) References Cited

OTHER PUBLICATIONS

Extended European Search Report for Application No. EP 07825594.0 dated Aug. 31, 2011.
Examination Report for Application No. JP 2009-523371 dated Sep. 26, 2012.
Response to Office Action for U.S. Appl. No. 12/308,045 dated Aug. 7, 2012.
Office Action for U.S. Appl. No. 12/308,045 dated Nov. 16, 2012.
Summons to Attend Oral Proceedings for Application No. EP 03711759.5 dated Jan. 4, 2012.
Summons to Attend Oral Proceedings for Application No. EP 06020381.7 dated Jan. 4, 2012.
Examination Report for Application No. AU 2008205325 dated Jun. 22, 2012.
Office Action for Application No. EP 08713076.1 dated Feb. 18, 2013.
Jizomoto, Hiroaki, "Phase Separation Induced in Gelatin-Base Coacervation Systems by Addition of Water-Soluble Nonionic Polymers I: Microencapsulation," Journal of Pharmaceutical Sciences, vol. 73, No. 7, 1984, pp. 879-882.
Office Action for U.S. Appl. No. 13/009,418 dated Jun. 21, 2013.
Office Action for U.S. Appl. No. 12/308,045 dated Oct. 7, 2013.
Office Action for U.S. Appl. No. 12/768,152 dated Jul. 25, 2013.
Office Action for Application No. JP 2009523371 dated Oct. 17, 2013.
Office Action for Application No. KR 1020097000087 dated Oct. 18, 2013 (English Translation).
Examination Report for CA Application No. 2,675,123 dated Apr. 15, 2014.
Examination Report, dated Aug. 25, 2014, for EP Application No. 08713076.1.
Second Office Action for MX Application No. MX/a/2009/007480 dated Apr. 15, 2014 (English Translation).

\* cited by examiner

VEGETARIAN MICROCAPSULES

CROSS REFERENCE TO RELATED APPLICATIONS

This application is the US National Phase application under 35 USC § 371 of PCT/US08/00301, filed on Jan. 9, 2008, and claims the benefit of priority to U.S. Provisional Application Nos. 60/879,636, filed on Jan. 10, 2007 and 60/879,759, filed on Jan. 10, 2007, both of which are incorporated by reference herein in their entireties.

BACKGROUND

Many microcapsules are small particles of solids or droplets of liquids inside a thin coating of a shell material such as beeswax, starch, gelatin, or polyacrylic acid. They are used, for example, to prepare liquids as free-flowing powders or compressed solids, to separate reactive materials, to reduce toxicity, to protect against oxidation and/or to control the rate of release of a substance such as an enzyme, a flavor, a nutrient, a drug, etc.

In the past, research has concentrated on microcapsules where each microcapsule had one core that contained a loading substance. However, one of the problems with single-core microcapsules is their susceptibility to rupture. Thus, others have tried to increase the thickness of the microcapsule wall in order to increase the strength and/or impermeability of such microcapsules. However, this practice can lead to a reduction in the loading capacity of the microcapsule.

Another approach to improve microcapsules has been to create microcapsules where each microcapsule had multiple chambers that each contained the loading substance. For example, U.S. Pat. No. 5,780,056 discloses a "multi-core" microcapsule having gelatin as a shell material. These microcapsules are formed by spray cooling an aqueous emulsion of oil or carotenoid particles such that the gelatin hardens around "cores" of the oil or carotenoid particles. Yoshida et al. (Chemical Abstract 1990:140735 or Japanese Patent Publication JP 01-148338) discloses a complex coacervation process for the manufacture of microcapsules in which an emulsion of gelatin and paraffin wax is added to an arabic rubber solution and then mixed with a surfactant to form "multi-core" microcapsules. Ijichi et al. (*J. Chem. Eng. Jpn.* (1997) 30(5):793-798) micoroencapsulated large droplets of biphenyl using a complex coacervation process to form multi-layered mirocapsules. U.S. Pat. Nos. 4,219,439 and 4,222,891 disclose "multi-nucleus" oil-containing microcapsules having an average diameter of 3-20 µm with an oil droplet size of 1-10 µm for use in pressure-sensitive copying papers and heat sensitive recording papers. U.S. Pat. Nos. 6,974,592 and 6,969,530 disclose multi-nucleus oil-containing microcapsules for delivery of various loading substances, like fish oil, to subjects.

Typically, the shell materials used to prepare such single- and multi-core microcapsules are by-products of animals. For example, gelatin, which has been used as a shell material for microcapsules, is often derived from the bones, skin, and cartilage of fish, swine, and/or cattle. While gelatin and other animal by-products are suitable microcapsule shell materials for many purposes, they are not suitable when one desires a microcapsule that is free of such animal by-products, such as for religious or dietary reasons. Therefore, there is a need in the art for microcapsules that have a high payload, are structurally strong, and are made from shell materials that are not by-products of animals. Disclosed herein are compositions and methods which meet these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to microcapsules with shells that are not animal by-products and methods for preparing and using such microcapsules. Also, in yet a further aspect, the disclosed subject matter relates to microcapsules with shells that are prepared from oppositely charged proteins. Methods of making and using the disclosed microcapsules are also enclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an omega-3 fatty acid" includes mixtures of two or more such fatty acids, reference to "the microcapsule" includes mixtures of two or more such microcapsules, and the like.

"Optional" or "optionally" means that the subsequently described event or circumstance can or cannot occur, and that the description includes instances where the event or circumstance occurs and instances where it does not. For example the phrase "adding a loading substance, a second polymer component, and, optionally, the composition, to the emulsion" includes instances where the composition is added to the emulsion and instances where the composition is not added to the emulsion.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

Reference herein to an "animal by-product" is meant to include compounds and materials that are derived from, isolated from, or purified from one or more parts of an animal's body (e.g., bones, skin, tissue, meat, cartilage, horns, hoofs, etc.). It is also meant to include compositions that are prepared by processing one or more animal by-products (e.g., derivatized, functionalized, or otherwise chemically or physically modified animal by-products). However, as used herein, an "animal by-product" is not meant to include milk or compounds that are derived from or isolated from animal milk, which is collected from a live animal. Further an "animal by-product" is not meant to include eggs or compositions derived from or isolated from eggs. The term "animal by-product" is also not meant to include synthetic materials, or materials derived from or isolated from plant, bacterial, fungal, or algal sources.

The term "vegetarian" generally refers to a diet lacking meat and/or animal by-products. It is recognized that there are various types of vegetarian diets. For example, a vegan or total vegetarian diet includes only foods from plants (e.g., fruits, vegetables, legumes, grains, seeds, and nuts). A lactovegetarian diet includes food from plants plus milk, cheese, and other dairy products. The ovo-lactovegetarian (or lacto-ovovegetarian diet) includes food from plants, milk, cheese, and other dairy products, and eggs. The semi-vegetarian diet excludes red meat but includes chicken and fish, along with foods from plants, milk, cheese, and other dairy products, and eggs. (USDA Dietary Guidelines for Americans, 2005). Unless specifically identified otherwise, the general term "vegetarian" as used herein includes each of the specific types of "vegetarian" diets mentioned above. Also, the phrase "suitable for a (particular vegetarian) diet" means that the particular shell material or microcapsule prepared therefrom would be acceptable for that particular vegetarian diet. For example, a material that is obtained from eggs would be suitable for an ovo-lactovegetarian diet (and also a semi-vegetarian diet, but not a lactovegetarian or vegan diet). As another example, a material that is derived from milk would be suitable for a lactovegetarian diet (and also an ovo-lactovegetarian diet and semi-vegetarian diet, but not a vegan diet). As yet another example, a material that is not derived from an animal by-product, milk, or eggs, would be suitable for a vegan diet, and for that matter a lactovegetarian, ovo-lactovegetarian, and semi-vegetarian diet as well. In still another example, a material that is derived from, say, fish would be suitable for a semi-vegetarian diet (but not a lactovegetarian, ovo-lactovegetarian, or vegan diet).

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Microcapsules

In certain examples, disclosed herein are microcapsules that comprise an agglomeration of primary microcapsules and a loading substance, each individual primary microcapsule having a primary shell, wherein the loading substance is encapsulated by the primary shell and the agglomeration is encapsulated by an outer shell, and wherein the primary shell and the outer shell are not animal by-products. These microcapsules are referred to herein as "multicore microcapsules." Also disclosed are "single-core" microcapsules that comprise a core, wherein the core comprises a loading substance, a primary shell surrounding the core, and an outer shell surrounding the primary shell, wherein the primary shell and the outer shell are not animal by-products. Unless stated otherwise, the term "microcapsule" is used herein to refer to multicore, single-core, or a mixture of multicore and single-core microcapsules. In these microcapsules (and others disclosed herein) the primary and outer shells comprise a non-animal by product, as is defined herein. Still further, disclosed are microcapsules comprising a loading substance and a polymer component, wherein the loading substance is surrounded by the polymer component, wherein the loading substance comprises a long chain polyunsaturated fatty acid, and wherein the polymer component is not an animal by-product.

Also, disclosed herein are microcapsules that comprise an agglomeration of primary microcapsules and a loading substance, each individual primary microcapsule having a primary shell, wherein the loading substance is encapsulated by the primary shell and the agglomeration is encapsulated by an outer shell, and wherein the primary shell and the outer shell are suitable for one or more of a vegan diet (e.g., the shells are not obtained from animal by-products, milk, or eggs), a lactovegetarian diet (e.g., the shells are not obtained from animal-by products or eggs, but can be obtained from milk), or a ovo-lactovegetarian diet (e.g., the shells are not obtained from animal-by products, but may be obtained from milk or eggs). In other examples, the primary and outer shells are suitable for a semi-vegetarian diet (e.g., the shells are obtained from fish).

Further, disclosed herein are microcapsules that comprise shells made from two oppositely charged proteins. That is, in the disclosed microcapsules the shell materials can be complex coacervates formed from two or more oppositely charged polymers. In certain particular examples, the oppositely charges polymers are both proteins. For example, disclosed herein are microcapsules where the shell materials (primary and/or outer shells) are complex coacervates form from a positively charged protein (such as whey, pea, or soy protein isolates or concentrates) and a negatively charged protein (such as caseinate) instead of a polyanionic polymer like gum aracaia.

The term "residue" as used herein refers to the moiety that is the resulting product of the specified chemical species in a particular reaction scheme or subsequent formulation or chemical product, regardless of whether the moiety is actually obtained from the specified chemical species. For example, an "amino acid residue" refers to the moiety which results when an amino acid participates in a particular reaction (e.g., the residue can be the product of an amino acid undergoing a transglutaminase catalyzed crosslinking reaction with another amino acid). In this case, the amino acid residue is "derived" from the amino acid. It is understood that this moiety can be obtained by a reaction with a species other than the specified amino acid, for example, by a reaction with a protein or peptide containing the amino acid, and the like. This concept applies to other chemical species disclosed herein, such as protein, saccharides like chitosan, lactose, and sucrose, and waxes. Thus, when such species undergo particular reactions or treatment (e.g., acid/base reactions, crosslinking reactions with other chemical species, and functional group transformations), they are referred to herein as a residue of the corresponding chemical species.

It is also contemplated that one or more additional shell layers can be placed on the outer shell of the microcapsules. The techniques described in International Publication No. WO 2004/041251 A1, which is incorporated by reference in its entirety, can be used to add additional shell layers to the microcapsules. It is understood, however, that the additional shell materials are not animal by-products.

Shell Materials

A number of different polymers can be used to produce the shell layers of the disclosed single-core and multicore microcapsules. For example, the primary shell and/or outer shell material of the disclosed microcapsules can comprise a protein, polyphosphate, polysaccharide, or mixtures thereof, which are not animal by-products. The disclosed microcapsules can contain shells that are coacervates of two oppositely charged polymers. For example, a polymer that is cationic or can be made cationic by adjustments in pH can be combined with a polymer that is anionic or can be made anionic by adjustments in pH to form a coacervate shell. In certain examples, the cationic polymers and anionic polymers are both proteins.

A particularly suitable shell material that is not an animal by-product as defined herein is whey protein. Whey protein typically comes in two major forms: isolate and concentrate. Unless specifically stated to the contrary the terms whey protein isolate and whey protein concentrate are included in the meaning of the term "whey protein." Whey protein concentrates contain fat, lactose, carbohydrates, and bioactive compounds. Whey protein isolates are processed to remove the fat, lactose, and carbohydrates, yet are usually lower in bioactive compounds as well. Generally speaking, whey protein isolate (WPI) is a collection of globular proteins that is isolated from whey, which is typically a by-product of cheese manufactured from bovine milk. In this sense, whey protein (isolates and concentrates) are suitable for lactovegetarian, ovo-lactovegtarian, and semi-vegetarian diets. WPI is a mixture of β-lactoglobulin (about 65%), α-lactoglobulin (about 25%), and serum albumin (about 8%), which are soluble in their native forms, independent of pH. WPI can be nearly 90% protein by weight. WPI can also include trace amounts of immunoglobulins IgG, IgA and IgM, glycomacropeptides, lactoferrin, lactoperoxidase, and/or lysozyme. WPI can be obtained from commercial sources such as NZMP ALACEN 895™ from Nealanders International Inc. (Rocky River, Ohio).

Another suitable shell material that is not an animal by-product as defined herein is soy protein, which includes soy protein concentrates and isolates. Soy protein isolates (SPI) is a highly refined or purified form of soy protein with a minimum protein content of about 90% on a dry basis. It is made from defatted soy flour, which has had most of the non-protein components, fats, and carbohydrates removed. It is typically used as a health food because it is a complete vegetable containing all the essential amino acids for growth. Also, it has a very low fat content when compared to animal sources of protein, such as meat or milk. SPI can be obtained from commercial sources such as PRO FAM 781™ from ADM Protein Specialties Division (Decatur, Ill.). Soy protein (isolates and concentrates) can be suitable for vegan, lactovegetarian, ovo-lactovegetarain, and semi-vegetarian diets.

Still another suitable shell material that is not an animal by-product as defined herein is pea protein, which includes pea protein concentrates and isolates. Pea protein can be obtained from a variety of species of pea. Pea protein isolates and concentrates can be obtained from commercial sources such as Roquette America, Inc., (Keokuk, Iowa) and Kirkman (Lake Oswego, Oreg.). Pea protein can be suitable for vegan, lactovegetarian, ovo-lactovegetarain, and semi-vegetarian diets.

Caseins are further examples of suitable shell materials that are not animal by-products. Caseins account for about 80% of the total protein in bovine milk, while whey proteins account for the remaining approximately 20%. Caseins are produced by precipitation with either acid at about pH 4.6 or rennet enzyme and the subsequent drying of the precipitate. Caseins are not typically coagulated by heat, do not denature, and are relatively hydrophobic. Caseinates are solubilized forms of casein produced by reaction with an alkaline substance. Common caseinates include: sodium caseinate, calcium caseinate, potassium caseinate, and ammonium caseinate. "Caseinates" is used herein to generally refer to these and other caseinates. Sodium caseinate is highly soluble and is used as an emulsifier in coffee whiteners, cottage cheese, cream liqueurs, yogurt, processed cheeses, and some meat products. Caseins and caseinates are commercially available and are suitable for lactovegetarian, ovo-lactovegetarain, and semi-vegetarian diets.

Egg white protein, which is a suitable shell material that is not an animal by-product as defined herein, also called albumin, is soluble in water, insoluble in alcohol or ether, and is used in food systems for foaming and gelation. On heating an aqueous solution of egg white protein to about 75° C., it becomes coagulated. Egg white protein can be suitable for ovo-lactovegetarain and semi-vegetarian diets.

Cereal prolamine proteins are still further examples of shell materials that are not animal by-products as defined herein. Cereal prolamine proteins are insoluble in water and anhydrous alcohol, and soluble in a mixture of the two. Zein, found in maize, is one of the most well understood plant proteins. It is clear, odorless, tasteless, hard, water-insoluble and edible, used as a coating for candy, nuts, fruit, pills, and other encapsulated foods and drugs, labeled as "confectioner's glaze" or as "vegetable protein", a very good water barrier, offering extended shelf-life, particularly under high-humidity and high-heat condition. Cereal prolamine proteins can be suitable for vegan, lactovegetarian, ovo-lactovegetarain, and semi-vegetarian diets.

Still another suitable shell material that is not an animal by-product as defined herein is agar. Agar is a polymer made up of subunits of galactose. It is a component of algae cell walls. It is a vegetarian substitute for gelatin and is even firmer and stronger than gelatin. Agar gels around 32-40° C. and remains solid up to about 85° C. Its major use is as a culture medium for microbiological work but another use is as a laxative. Agar performs well during complex coacervates as a polyanion. Agar can be obtained from commercial sources such as AGAR RS-100™ from TIC Gums (Belcamp, Md.). Agar can be suitable for vegan, lactovegetarian, ovo-lactovegetarain, and semi-vegetarian diets.

Gellan gum is another suitable shell material that is not an animal by-product as defined herein and can be used in the compositions and methods disclosed herein. Gellan gum is a vegetarian gelatin substitute and is a polysaccharide produced by the bacterium *Sphingomonas elodea*, which is soluble in water. It is used primarily as an alternative to agar as a gelling agent in microbiological culture. In certain applications, gellan gum can be more desirable than agar because it has better visual clarity and strength and it is able to withstand temperatures of about 120° C.; thus, it is safe during spray-drying processes. Also, one needs only approximately half the amount of gellan gum as agar to reach an equivalent gel strength, though the exact texture and quality depends on the concentration of divalent cations present. As a food additive, gellan gum is used as a thicker, emulsifier and stabiliser. Gellan gum can be obtained from commercial sources such as from KELCOGEL F™ from C.P. Kelco (San Diego, Calif.). Gellan gum can be suitable for vegan, lactovegetarian, ovo-lactovegetarain, and semi-vegetarian diets.

Gum arabic is yet another suitable shell material that is not an animal by-product as disclosed herein and can be used in the compositions and methods disclosed herein. Gum arabic is a substance is taken from two sub-Saharan species of the acacia tree, *Acacia senegal* and *Acacia seyal*. It is used primarily in the food industry as a stabilizer, but has had more varied uses in the past, including viscosity control in inks. Its E number is E-414. Gum arabic is a complex mixture of saccharides and glycoproteins, and it is edible. It is an ingredient in soft drink syrups, "hard" gummy candies like gumdrops, marshmallows, and most notably, chewing gums. For artists it is the traditional binder used in watercolor paint, and was used in photography for gum printing. Pharmaceuticals and cosmetics also use gum arabic. Gum Arabic can be obtained from commercial sources such as TIC gums (Belcamp, Md.).

Xanthan gum is still another suitable shell material that is not an animal by-product as defined herein. Xanthan gum is a natural gum polysaccharide as a food additive and rheology modifier. It is produced by a biotechnological process involving fermentation of glucose or sucrose by *Xanthomonas campestris*. One of the properties of xanthan gum is its capability of producing a large increase in the viscosity by adding a very small quantity of gum (e.g., on the order of one percent). In most foods, it is used at 0.5% or as low as 0.05%. The viscosity of xanthan gum solutions decreases with higher shear rates. Like other gums it is very stable under a wide range of temperatures and pH. Xanthan gum is commercially available. Xanthan gum can be suitable for vegan, lactovegetarian, ovo-lactovegetarain, and semi-vegetarian diets.

Pectin is yet another suitable shell material that is not an animal by-product as defined herein. Pectin is a grouping of acid structural polysaccharides found in fruit and vegetables and is prepared mainly from citrus peel waste and apple pomace. Pectin can be used as a replacement for polyphosphate, which has been used as a shell material, because it is abundant and relatively inexpensive. Amidated pectin is suitable gelatin replacement or supplement because it also has amine portions on its structure that can be crosslinked by mechanisms similar to that used for gelatin. This allows for a quicker development cycle compared to having to develop a new technology or modification of current technology. Low-methoxyl-pectin is also a suitable shell material. Pectin and low-methoxyl pectin can be suitable for vegan, lactovegetarian, ovo-lactovegetarain, and semi-vegetarian diets.

Further examples of suitable shell materials include, but are not limited to, polyphosphate, alginate, chitosan, carrageenan, starch, modified starch, oligofructans, konnyaku, alpha-lactalbumin, beta-lactoglobumin, ovalbumin, polysorbiton, maltodextrin (DE18, DE 21, DE40 etc.), cyclodextrins (alpha-, beta- and gamma-cyclodextrins), cellulose, cellulose ether, methyl cellulose, ethyl cellulose, hydropropylmethylcellulose, carboxymethylcellulose, hydroxypropyl cellulose, milk protein, canola protein, albumin, chitin, polylactides, poly-lactide-co-glycolides, derivatized chitin, poly-lysine, dilutan gum, locus bean gum, welan gum, and xanthan gum including combinations and mixtures thereof. It is also contemplated that derivatives of these polymers can be used as well.

The shell material can be a two-component system made from a mixture of different types of polymer components, and where a composition has been added to the system to improve impermeability. In other examples, the shell material can be a complex coacervate between two or more polymer components (e.g., whey or soy protein isolate and agar). Component A can be whey or soy protein isolate, although other polymers like those mentioned above for the shell materials are also contemplated as component A. Component B can be agar, gellan gum, pectin, low methoxyl pectin, gum arabic, alginate, chitosan, carrageenan, carboxymethyl-cellulose or a mixture thereof. Again other polymers like those disclosed above for the shell materials are also contemplated as component B. The molar ratio of component A:component B that is used depends on the type of components but is typically from about 1:5 to about 15:1. For example, when whey or soy protein isolate and agar are used as components A and B respectively, the molar ratio of component A:component B can be about 8:1 to about 12:1; when whey or soy protein isolate and gellan gum are used as components A and B respectively, the molar ratio of component A:component B can be about 2:1 to about 1:2; and when whey or soy protein isolate and low methoxyl pectin are used as components A and B respectively, the molar ratio of component A:component B can be about 3:1 to about 5:1. In many of the disclosed microcapsules the primary shell and/or outer shell can comprise a complex coacervate. For example, the primary shell and/or outer shell can comprise a complex coacervate of whey, pea, or soy protein isolate and agar and/or gellan gum. In other examples, the primary and/or outer shell can comprise a complex coacervate of whey, pea, or soy protein isolate and a caseinate (e.g., sodium, calcium, potassium, or ammonium caseinate).

In particular examples, using WPI, PPI, or SPI and agar to prepare primary microcapsules, and having gellan gum deposit on the surface of the primary microcapsules to form an outer shell, results in stable non-gelatin or vegetarian microcapsules without the need for any transglutaminase crosslinking. Likewise, using WPI, PPI, or SPI and gum arabic or caseinate can result in compact microcapsules with long induction periods. Further, the use of such shell materials can lower costs significantly since transglutaminase is expensive and requires long production time.

In the disclosed microcapsules the outer shell can have an average diameter of from about 1 µm to about 2,000 µm, from about 20 µm to about 1,000 µm, or from about 30 µm to about 80 µm. In further examples, the average diameter of the outer shell can be about 1, 10, 20, 30, 40, 50, 60, 70, 80, 90, 200, 300, 400, 500, 600, 700, 800, 900, 1000, 1200, 1300, 1400, 1500, 1600, 1700, 1800, 1900, or 2000 µm, where any of the stated values can form an upper or lower endpoint when appropriate.

The primary shells of the disclosed microcapsules can have an average diameter of from about 40 nm to about 10 µm or from about 0.1 µm to about 5 µm. In further examples, the average diameter of the primary shell can be about 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, 2 µM, 3 µm, 4 µm, 5 µm, 6 µm, 7 µm, 8 µm, 9 µm, 10 µm, where any of the stated values can form an upper or lower endpoint when appropriate. Particle size can be measured using any typical equipment known in the art, for example, a COULTER™ LS230 Particle Size Analyzer, Miami, Fla., USA.

Loading Substances

In the disclosed microcapsules, the loading substance can be any substance that one desires to be microencapsulated (e.g., a substance that one desired to be delivered to a subject). In many examples, a suitable loading substance is not entirely soluble in an aqueous mixture. The loading substance can be a solid, a hydrophobic liquid, or a mixture of a solid and a hydrophobic liquid. In many of the examples herein, the loading substance can comprise a long chain polyunsaturated fatty acid, specific examples of which are included below. Further, the loading substance can comprise a biologically active substance, a nutrient such as a nutritional supplement, a flavoring substance, a polyunsaturated fatty acid like an omega-3 fatty acid, a vitamin, a mineral, a carbohydrate, a steroid, a trace element, and/or a protein, and the like including mixtures and combinations thereof. In other examples, the loading substance can comprise microbial oil, algal oil (e.g., oil from a dinoflagellate such as *Crypthecodinium cohnii*), fungal oil (e.g., oil from *Thraustochytrium, Schizochytrium*, or a mixture thereof), and/or plant oil (e.g., flax, vegetables), including mixtures and combinations thereof. In other examples, the loading substance can be a pharmaceutical composition (e.g., a drug and/or an enzyme) or a flavor. The loading substance can also be a hydrophobic liquid, such as grease, oil or a mixture thereof. Typical oils can be fish oils, vegetable oils (e.g., canola, olive, corn, rapeseed), mineral oils, derivatives thereof or mixtures thereof. The loading substance can comprise a purified or partially purified oily substance such as a fatty acid, a triglyceride, or a mixture thereof.

In still other examples, a suitable loading substance can comprise marine oil, such as natural and refined and concentrated fish oil. Examples of suitable fish oils include, but are not limited to, Atlantic fish oil, Pacific fish oil, Mediterranean fish oil, light pressed fish oil, alkaline treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, and shark oil, including mixtures and combinations thereof. Non-alkaline treated fish oil is also a suitable loading substance. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed delivery devices and in the disclosed food articles and methods.

Many of the microbial, algal, fungal, plant, and marine oils disclosed herein contain omega-3 fatty acids. As such, certain delivery devices disclosed herein can contain a loading substance that comprises an omega-3 fatty acid, an alkyl ester of an omega-3 fatty acid, a triglyceride ester of an omega-3 fatty acid, a phytosterol ester of an omega-3 fatty acid, and/or mixtures and combinations thereof. An omega-3 fatty acid is an unsaturated fatty acid that contains as its terminus $CH_3$—$CH_2$—$CH$=$CH$—. Generally, an omega-3 fatty acid has the following formula:

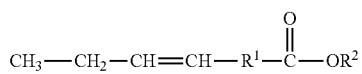

wherein $R^1$ is a $C_3$-$C_{40}$ alkyl or alkenyl group comprising at least one double bond and $R^2$ is H or alkyl group. The term "alkane" or "alkyl" as used herein is a saturated hydrocarbon group (e.g., methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like). The term "alkene" or "alkenyl" as used herein is a hydrocarbon group containing at least one carbon-carbon double bond. Asymmetric structures such as (AB)C=C(CD) are intended to include both the E and Z isomers (cis and trans). In a further example, $R^1$ can be a $C_5$-$C_{38}$, $C_6$-$C_{36}$, $C_8$-$C_{34}$, $C_{10}$-$C_{32}$) $C_{12}$-$C_{30}$, $C_{14}$-$C_{28}$, $C_{16}$-$C_{26}$, or $C_{18}$-$C_{24}$ alkenyl group. In yet another example, the alkenyl group of $R^1$ can have from 2 to 6, from 3 to 6, from 4 to 6, or from 5 to 6 double bonds. Still further, the alkenyl group of can have from 1, 2, 3, 4, 5, or 6 double bonds, where any of the stated values can form an upper or lower endpoint as appropriate.

Specific examples of omega-3 fatty acids that are suitable loading substances that can be used in the disclosed delivery devices include, but are not limited to, α-linolenic acid (18:3ω3), octadecatetraenoic acid (18:4ω3), eicosapentaenoic acid (20:5ω3) (EPA), eicosatetraenoic acid (20:4ω3), henicosapentaenoic acid (21:5ω3), docosahexaenoic acid (22:6ω3) (DHA), docosapentaenoic acid (22:5ω3) (DPA), including derivatives and mixtures thereof. Many types of fatty acid derivatives are well known to one skilled in the art. Examples of suitable derivatives are esters, such as phytosterol esters, furanoid esters, branched or unbranched $C_1$-$C_{30}$ alkyl esters, branched or unbranched $C_2$-$C_{30}$ alkenyl esters or branched or unbranched $C_3$-$C_{30}$ cycloalkyl esters, in particular phytosterol esters and $C_1$-$C_6$ alkyl esters. In a further example, the loading substance can be a phytosterol ester of docosahexaenoic acid and/or eicosapentaenoic acid, a $C_1$-$C_6$ alkyl ester of docosahexaenoic acid and/or eicosapentaenoic acid, a triglyceride ester of docosahexaenoic acid and/or eicosapentaenoic acid, and/or a mixture thereof.

Other examples of suitable loading substances that can be present in the disclosed delivery devices comprise at least 4, at least 6, at least 8, at least 10, at least 12, at least 14, at least 16, at least 18, or at least 20 carbon atoms. In some other examples, the loading substance can contain about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In still other examples, the loading substance can comprise a mixture of fatty acids (including derivatives thereof) having a range of carbon atoms. For example, the loading substance can comprise from about 8 to about 40, from about 10 to about 38, from about 12 to about 36, from about 14 to about 34, from about 16 to about 32, from about 18 to about 30, or from about 20 to about 28 carbon atoms.

Some further examples of loading substances are those that contain at least one unsaturated bond (i.e., a carbon-carbon double or triple bond). For example, the loading substance can contain at least 2, at least 3, at least 4, at least 5, at least 6, at least 7, or at least 8 carbon-carbon double bonds, triple bonds, or any combination thereof. In another example, the loading substance can comprise 1, 2, 3, 4, 5, 6, 7, or 8 unsaturated bonds, where any of the stated values can form an upper or lower endpoint as appropriate.

Some specific examples of loading substances, which are unsaturated fatty acids, are shown in the following tables. Derivatives of these fatty acids are also suitable and are thus contemplated herein.

TABLE 1

Examples of Monoene Acids

| Total number of carbon atoms in the fatty acid chain | Carbon number where double bond begins. ("c" denotes a cis double bond; "t" denotes a trans double bond) |
| --- | --- |
| 10 | 4c |
| 12 | 4c |
| 14 | 4c and 9c |
| 16 | 3t, 4c, 5t, 6c, 6t, 9c (palmitooleic), and 11c |
| 18 | 3t, 5c, 5t, 6c (petroselinic), 6t, 9c (oleic), 10c, 11c (cisvaccenic), 11t (vaccenic), and 13c |
| 20 | 5c, 9c (gadolenic), 11c, 13c, and 15c |
| 22 | 5c, 11c (cetoleic), 13c (erucic), and 15c |
| 24 | 15c (selacholeic, nervonic) |
| 26 | 9c, and 17c (ximenic) |
| 28 | 9c, 19c (lumequic) |
| 30 | 21c |

Unsaturated fatty acids that contain at least one pair of methylene interrupted unsaturated bonds are also suitable loading substances. By "methylene interrupted unsaturated bond" is meant that one carbon-carbon double or triple bond is separated from another carbon-carbon double or triple bond by at least one methylene group (i.e., $CH_2$). Specific examples of such loading substances include, but are not limited to, the n-1 family derived from 9, 12, 15-16:3; n-2 family derived from 9, 12, 15-17:3, 15:3, 17:3, 17:4, 20:4; n-3 family derived from 9, 12, 15-18:3, 15:2, 15:3, 15:4, 16:3, 16:4, 18:3 (α-linolenic); 18:4, 18:5, 20:2, 20:3, 20:4; 20:5 (EPA), 21:5, 22:3, 22:5 (DPA), 22:6 (DHA), 24:3, 24:4, 24:5, 24:6, 26:5, 26:6, 28:7, 30:5; n-4 family derived from 9, 12-16:2, 16:2, 16:3, 18:2, 18:3; n-5 family derived from 9, 12-17:2, 15:2, 17:2, 17:3, 19:2, 19:4, 20:3, 20:4 21:4, 21:5; n-6 family derived from 9, 12-18:2, 15:2, 16:2, 18:2 (linoleic acid), 18:3 (γ-linolenic); 20:2, 20:3, 20:4 (arachidonic acid), 22:2, 22:3, 22:4 (adrenic acid), 22:5, 24:2, 24:4, 25:2, 26:2, 30:4; n-7 family derived from 9-16:1, 15:2, 16:2, 17:2, 18:2, 19:2; n-8 family derived from 9-17:1, 15:2, 16:2, 17:2, 18:2, 19:2; n-9 family derived from 9-18:1, 17:2, 18:2, 20:2, 20:3, 22:3, 22:4; n-11 family 19:2, and the n-12 family 20:2. In one particular specific example, the loading substance can comprise arachidonic acid.

In the above paragraph (and throughout) the compounds are identified by referring first to the "n-x family," where x is the position in the fatty acid where the first double bond begins. The numbering scheme begins at the terminal end of the fatty acid, where, for example, the terminal $CH_3$ group is designated position 1. In this sense, the n-3 family would be an omega-3 fatty acid, as described above. The next number identifies the total number of carbon atoms in the fatty acid. The third number, which is after the colon, designates the total number of double bonds in the fatty acid. So, for example, in the n-1 family, 16:3, refers to a 16 carbon long fatty acid with 3 double bonds, each separated by a methylene, wherein the first double bond begins at position 1, i.e., the terminal end of the fatty acid. In another example, in the n-6 family, 18:3, refers to an 18 carbon long fatty acid with 3 methylene separated double bonds beginning at position 6, i.e., the sixth carbon from the terminal end of the fatty acid, and so forth.

Further examples of loading substances that contain at least one pair of methylene interrupted unsaturated bonds are shown in Table 2.

TABLE 2

Examples of Polyene Acids

| Total number of carbon atoms in the fatty acid chain | Carbon number where double bond begins. ("c" denotes a cis double bond; "t" denotes a trans double bond) |
|---|---|
| 18 | 5, 9 |
|  | 5, 11 |
|  | 2t, 9, 12 |
|  | 3t, 9, 12 |
|  | 5t, 9, 12 |
|  | 5, 9, 12 |
|  | 5, 11, 14 |
|  | 3t, 9, 12, 15 |
|  | 5, 9, 12, 15 |
| 20 | 5, 11 |
|  | 5, 13 |
|  | 7, 11 |
|  | 7, 13 |
|  | 5, 11, 14 |
|  | 7, 11, 14 |
|  | 5, 11, 14, 17 |
| 22 | 5, 11 |
|  | 5, 13 |
|  | 7, 15 |
|  | 7, 17 |
|  | 9, 13 |
|  | 9, 15 |

Specific examples of suitable loading substances that contain conjugated unsaturated bonds include, but are not limited to, those in Table 3. By "conjugated unsaturated bond" is meant that at least one pair of carbon-carbon double and/or triple bonds are bonded together, without a methylene ($CH_2$) group between them (e.g., —CH═CH—CH═CH—).

TABLE 3

Examples of Conjugated Polyene Acids

| Total number of carbon atoms in the fatty acid chain. | Carbon number where double bond begins. ("c" denotes a cis double bond; "t" denotes a trans double bond) |
|---|---|
| 10 | 2t, 4t, 6c |
|  | 2c, 4t, 6t |
|  | 3t, 5t, 7c |
|  | 3c, 5t, 7t |
| 12 | 3, 5, 7, 9, 11 |
| 14 | 3, 5, 7, 9, 11 |

TABLE 3-continued

Examples of Conjugated Polyene Acids

| Total number of carbon atoms in the fatty acid chain. | Carbon number where double bond begins. ("c" denotes a cis double bond; "t" denotes a trans double bond) |
|---|---|
| 18 | 10t, 12t |
|  | 8c, 10t, 12c (jacaric) |
|  | 8t, 10t, 12c (calendic) |
|  | 8t, 10t, 12t |
|  | 9t, 11t, 13c (catalpic) |
|  | 9c, 11t, 13t (α-eleostearic) |
|  | 9c, 11t, 13c (punicic) |
|  | 9t, 11t, 13t (β-eleostearic) |
|  | 9c, 11t, 13t, 15c (α-parinaric) |
|  | 9t, 11t, 13t, 15t (β-parinaric) |

In the above examples of suitable loading substances, derivatives of the disclosed loading substances can also be used. By "derivatives" is meant the ester of a fatty acid (e.g., methyl and ethyl esters), salts of the fatty acids (e.g., sodium and potassium salts), and triglycerides, diglycerides, and monoglycerides, sterol esters, antioxidant-oil conjugates (e.g., ascorbyl palmitate), and naturally derivatives such as furanoid fatty acid derivatives.

The loading substances disclosed herein can also be crude oils, semi-refined (also called alkaline refined), or refined oils from such sources disclosed herein. Still further, the disclosed compositions and methods can use oils comprising re-esterified triglycerides.

It is contemplated herein that one or more of the disclosed loading substances can be used. For example the disclosed delivery devices can contain two or more different loading substances. Further, the loading substance can be present in an amount of from about 1% to about 50% by weight of a microcapsule. In specific examples, the loading substance can be present in an amount of from about 1% to about 40%, from about 1% to about 30%, from about 1% to about 20%, from about 1% to about 15%, or from about 1% to about 10% by weight of a microcapsule.

In one example, the loading substance is not a fatty acid conjugate. A fatty acid conjugate is a fatty acid that has been coupled to (e.g., bonded to) another chemical moiety, such as a metal (e.g., chromium) or cofactor ($CoQ_{10}$). In other examples, the loading substance is not oil with a low interfacial tension (IT) (i.e., having an interfacial tension of less than about 15 dynes/cm). In other examples, the loading substance is such a fatty acid conjugate or low IT oil.

In one example, the loading substances can be or can contain an antioxidant. Suitable examples of antioxidants include, but are not limited to, a phenolic compound, a plant extract, or a sulfur-containing compound. In certain examples disclosed herein the antioxidant can be ascorbic acid or a salt thereof, e.g., sodium ascorbate. In other examples, the antioxidant can be citric acid or a salt thereof. In still other examples, the antioxidant can be vitamin E, $CoQ_{10}$, lutein, zeaxanthan, carotene (e.g., beta-carotene) tocopherols, lipid soluble derivatives of more polar antioxidants such as ascobyl fatty acid esters (e.g., ascobyl palmitate), plant extracts (e.g., rosemary, sage and oregano oils), algal extracts, and synthetic antioxidants (e.g., BHT, TBHQ, ethoxyquin, alkyl gallates, hydroquinones, tocotrienols), or mixtures thereof.

The disclosed loading substance can also be or contain other nutrient(s) such as vitamins other trace elements (e.g., zinc), minerals, and the like. Further, the loading substances can comprise other components such as preservatives, antimicrobials, anti-oxidants, chelating agents, thickeners, flavorings, diluents, emulsifiers, dispersing aids, or binders, including any mixture thereof.

In addition, the loading substance can have a low interfacial tension. For example, a suitable loading substance can have an interfacial tension of less than about 20, less than about 15, less than about 11, less than about 9, less than about 7, or less than about 5 dynes/cm. In other examples, the loading substance can have an interfacial tension of from about 0.1 to about 20, from about 1 to about 15, from about 2 to about 9, from about 3 to about 9, from about 4 to about 9, from about 5 to about 9, or from about 2 to about 7 dynes/cm. In still further examples, the loading substance can have an interfacial tension of about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0, where any of the stated values can form an upper or lower endpoint when appropriate. In particular examples, the loading substance can be an algal oil with an interfacial tension of about 0.5, 0.6, 0.7, 0.8, 0.9, or 1.0 dynes/cm. The loading substance can also be a fungal oil with an interfacial tension of about 3.0, 3.1, 3.2, 3.3, or 3.4 dynes/cm.

The interfacial tension of a loading substance can be determined by methods known in the art. For example, the interfacial tension from a loading substance to a standard gelatin solution or from a loading substance to distilled water can be determined with a Fisher Surface Tensiomat. Generally, a standard gelatin solution or distilled water can be poured into a sample vessel, which is placed on the sample table of a tensiomat. The loading substance can then be added to the sample vessel. The sample can be raised so that the ring of the tensiomat is immersed in the loading substance. The interfacial tension is the measure of downward force on the ring as it passes through the interface of the loading substance and standard gelatin solution or the interface of the loading substance and distilled water, depending on whichever experimental setup is being used.

The interfacial tension measurements disclosed herein for the loading substances refer to values determined as just described using a standard gelatin solution (50° C.) that contains 3.3% (w/w) of 240 Bloom kosher fish gelatin (e.g., from LAPI, Tuscany, Italy), 0.5% (w/w) sodium ascorbate, and 0.33% (w/w) polyphosphate solution dissolved in distilled water.

Further, the payloads of loading substances in the disclosed microcapsules can be from about 20% to about 90%, about 50% to about 70% by weight, or about 60% by weight of the microcapsule. In other examples, the disclosed microcapsules can contain about 20, 25, 30, 35, 40, 45, 50, 55, 60, 65, 70, 75, 80, 85, or 90% by weight of the microcapsule, where any of the stated values can form an upper or lower endpoint when appropriate.

SPECIFIC EXAMPLES

Specific examples of microcapsules that contain any of the shell materials and any of the loading substances are disclosed herein. Some specific examples include, but are not limited to, microcapsules where the shell materials are complex coacervates, e.g., coacervates of whey protein isolates and agar, gellan gum, gum arabic, caseinate, and/or low methoxyl pectin. In another example, the microcapsules can have shell materials that are complex coacervates of soy protein isolates and agar, gellan gum, gum arabic, caseinate, and/or low methoxyl pectin. In still another example, the microcapsules can have shell materials that are complex coacervates of pea protein isolate and agar, gellan gum, gum arabic, caseinate, and/or low methoxyl pectin. Loading substances that can be used can, in many instances, include marine oils (e.g., fish oils and algal oils). Loading substances that comprise omega-3 fatty acids such as EPA and DHA can also be desirable. Further, derivatives of omega-3 fatty acids, such as mono-, di-, and triglycerides, alkyl esters, sterol esters, antioxidant esters (e.g., ascorbyl and citryl esters), and furanoid esters, can also be suitable loading substances.

Some particularly suitable microcapsules include microcapsules containing fish oils. Examples of such fish oils include, but are not limited to, sardine, anchovy, bonito, and/or tuna oil. Fish oils can also be referred to herein by the approximate ratio of EPA and DHA, or derivatives thereof, found in the oil. For example, 18:12 oils generally comprise a ratio of EPA to DHA (or their triglyceride esters for example) of about 18:12. Likewise, 5:25 oils generally comprise a ratio of EPA to DHA of about 5:25. Such microcapsules can be Generally Regarded as Safe (GRAS), kosher, and/or Halal. Further, such microcapsules can contain algal oils comprising omega-3 fatty acids. In this case, the microcapsules can be regarded as organic, vegetarian, and/or vegan, depending on the particular shell material and the particular standards for classifying such materials. Also, such microcapsules can have at least about 130 mg of DHA or at least about 150 mg of EPA and DHA per gram of powder. Further, antioxidants such as ascorbic acid, citric acid, and/or phosphoric acid (or salts thereof) can be present in such microcapsules.

Emulsions

Also disclosed herein are emulsions that comprise a first polymer component and a loading substance, wherein the loading substance comprises a long chain polyunsaturated fatty acid and wherein the first polymer component is not an animal by-product. Any of the loading substances disclosed herein can be used. For example the loading substance can comprise an omega-3 fatty acid. The loading substance can comprise a marine oil. The loading substance can comprise a fish oil. Also, the loading substance can comprise an algal oil.

Suitable polymer components for the disclosed emulsions can be any of those disclosed herein that are not animal by-products. Many examples of these are mentioned elsewhere herein.

Method of Making Microcapsules

Several variables affect the processes of preparing microcapsules in general, for example, the type of shell material, charge density, concentration, the ratio of various shell materials, a shell material's molecular weight (Mw) and distribution, the pH and temperature of the system, and microion concentration. In the methods disclosed herein, a non-animal by-product is used as a shell material(s). Many suitable non-animal by-products are disclosed herein, and they often behave differently when used to prepare microcapsules as compared to animal derived shell materials. For example, most vegetable proteins are globular and are different that animal derived gelatins in terms of molecular weight, structure, amino acid composition, charge density, and the like. Gelatin is a protein that can form thermoreversible gels through the formation of hydrogen-bond-stabilized triple helices as the gelatin solution is cooled. Vegetable proteins, like soy proteins, are more rigid in structure, more heat-stable compared to gelatin, and denature under prolonged heating, especially above 85° C. Their amino acid compositions are different, too. See e.g., Table 4.

TABLE 4

| | Acidic processed gelatin (Gelatin Type A) | Soy protein |
|---|---|---|
| Isoelectric point | About pH 9 | 7s . . . about pH 4.8 |
| | | 11s . . . about pH 6.4 |
| MW | 100 kDa | 7s . . . 180 kDa |
| | | 11s . . . 360 kDa |
| Glutamic % | 11.3 | 17.5 |
| Lysine % | 4.5 | 5.6 |
| Proteinogenic average | 9.8 | 7.0 |

So, soy proteins require different pH, temperature, concentration, ratio of polyelectrolytes and microion concentration than gelatin for forming microcapsules via complex coacervation. Also, because soy proteins contain more glutamate and lysine residues than gelatin, they are potentially more active than gelatin for the cross-linking reaction by transglutaminase, which catalyzes the acyl transfer reaction between glutaminyl residues and primary amines. Thus, vegetable proteins microcapsules can be thermal crosslinked by heating up to about 80° C. Similar considerations also apply when using whey or pea proteins, agar, alginates, gellan gum, gum arabic, xanthan gum, cesains, and other shell materials that are disclosed herein that are not animal by-products.

Since vegetable proteins are not typically cold setting gelling agents, vegetarian gelatin substitutes, such as pectin, agar, gellan gum, gum arabic, and alginate, can be used as anionic polysaccharides to prepare vegetarian microcapsule shells through complex coacervation with soy proteins. Caseinates or other anionic proteins can also be used instead of anionic polysaccharides. Again, these vegetarian gelatin substitutes are different to polyanions use for preparing gelatin microcapsules in terms of charge density, molecular weight and molecular weight distribution. Consequently, they require different concentration, microion concentration, pH, and temperature during complex coacervation with vegetable proteins.

Microcapsules prepared by the processes disclosed herein typically have a combination of payload and structural strength that are suitable for food articles, supplements, formulation vehicles, and methods disclosed herein. In one example, the methods disclosed in U.S. Pat. Nos. 6,974,592 and 6,969,530, and US Publication No. 2005-0019416-A1, which are incorporated by reference in their entirety, can be used to prepare microcapsules. It is also contemplated that one or more additional shell layers can be placed on the outer shell of the single-core or multicore microcapsules. In one example, the techniques described in International Publication No. WO 2004/041251 A1, which is incorporated by reference in its entirety, can be used to add additional shell layers to the single-core and multi-core microcapsules.

In general, suitable microcapsules can be prepared by a process that comprises providing an emulsion comprising a first polymer component a loading substance, and a second polymer component, wherein the first and second polymer components do not comprise animal by-products; adjusting pH, temperature, concentration, mixing speed, or a combination thereof to form an aqueous mixture comprising a primary shell material, wherein the primary shell material comprises the first and second polymer components and surrounds the loading substance; cooling the aqueous mixture to a temperature above the gel point of the primary shell material until the primary shell material forms agglomerations; and further cooling the aqueous mixture to form an outer shell around the agglomeration. In a further example, the agglomeration can be contacted with a third polymer component; adjusting the pH, temperature, concentration, mixing speed, or a combination thereof to form an additional outer shell around the agglomeration. This process can be a two step process, i.e., the first polymer component and loading substance can be emulsified and then the second polymer component can be added. Alternatively, this process can be a one step process, i.e., the first and second polymer components and the loading substance can be emulsified together.

In these methods, the first polymer component, second polymer component, and third polymer component can be the same as any of the primary and outer shell materials described herein. That is, the first, second, and third polymer components can become the primary and/or outer shell materials in the disclosed methods for preparing microcapsules. Furthermore, any of the loading substances described herein can be used in these methods for preparing microcapsules.

In the disclosed methods, an aqueous mixture of a loading substance, a first polymer component of the shell material, and a second polymer component of the shell material is formed. The aqueous mixture can be a mechanical mixture, a suspension, or an emulsion. When a liquid loading substance is used, particularly a hydrophobic liquid, the aqueous mixture can be an emulsion of the loading substance and the polymer components. In another example, a first polymer component is provided in aqueous solution, optionally with processing aids, such as antioxidants. A loading substance can then be dispersed into the aqueous mixture, for example, by using a homogenizer. If the loading substance is a hydrophobic liquid, an emulsion is formed in which a fraction of the first polymer component begins to deposit around individual droplets of loading substance to begin the formation of primary shells. If the loading substance is a solid particle, a suspension is formed in which a fraction of the first polymer component begins to deposit around individual particles to begin the formation of primary shells. At this point, another aqueous solution of a second polymer component can be added to the aqueous mixture (or alternatively, the aqueous mixture can be added to the aqueous solution of the second polymer component).

In the processes for preparing microcapsules disclosed herein, providing an emulsion of the first polymer component and the loading substance can be accomplished by methods and apparatus known in the art, e.g., homogenization and high pressure/high shear pumps. For example, emulsification can take place by emulsifying at from about 1,000 to about 15,000 rpm. The emulsification step can be monitored by removing a sample of the mixture and analyzing it under such methods as microscopy, light scattering, turbidity, etc. Generally, emulsification can be performed until an average droplet size of less than about 1,000, 750, 500, 100, or 10 nm is obtained. Not wishing to be bound by theory but it is believed that by varying the emulsification speed it is possible to produce single or multi-core microcapsules. For example, when lower emulsification speeds are used (e.g., 1,000 to 2,000 rpm), the droplets of the loading substance are large enough to form a single particle, which upon encapsulation, produces a single core microcapsule. Conversely, if high emulsification speeds are used (e.g., 5,000 to 15,000 rpm), the resultant droplets of loading substance are usually small (e.g., from 1 to 10 µm). These tiny droplets can have higher surface energy and can readily form agglomerations when pH and/or temperature is adjusted accordingly, which results in the formation of multi-core microcapsules upon encapsulation. Particle size can be measured using any typical equipment known in the art, for example, a COULTER™ LS230 Particle Size Analyzer, Miami, Fla. USA.

The emulsification step can be performed at less than or greater than room temperature, e.g., at 4, 10, 15, 20, 30, 37, 40, 50, 60, 70, or 80° C., where any of the stated values can form an upper or lower endpoint when appropriate. Specific examples include emulsifying the mixture at from about 10° C. to about 60° C. or from about 30° C. to about 50° C.

It is further contemplated that antioxidants and/or surfactants, which are also described herein, can be added to the emulsion and/or aqueous mixture. Such antioxidants and/or surfactants can be added before, during, and/or after the emulsion is provided. Further, in the whole system involving the loading substance, shell materials, antioxidants, and additional compositions, the antioxidative capacity is at a certain level when the amount of antioxidants used is given. Therefore, in the methods for preparing microcapsules disclosed herein, purging with inert gas such as nitrogen during any or all of emulsification, mixing, coacervation, and or cooling processes can prevent the consumption of antioxidants by oxygen from air, and delay oxidation of the loading substance during storage. It can also prevent the formation of off-flavor compounds due to oxidation in the microencapsulation process.

Also contemplated is that chelators can be added to the emulsion and/or aqueous mixture. Autoxidation of lipids is catalyzed by metal ions, particularly iron and copper ions. Thus, chelating of the metal ions can help retard the oxidation and extend its "lag phase," therefore extending the shelf-life of bulk oil or encapsulated oils. Like antioxidants, the chelators can be added before, during and/or after the emulsion is provided. Examples of suitable chelators include, but are not limited to are disodium ethylenediamine tetraacetic acid, which is one of the most frequently used chelating agents in food processing, citric acid, phytic acid, malic acid, tartaric acid, oxalic acid, succinic acid, polyphosphoric acids etc.

The amount of the first and second polymer components of the shell material provided in the aqueous mixture is typically sufficient to form both the primary shells and the outer shells of the loading agglomeration of microcapsules. The loading substance can be provided in an amount of from about 1% to about 15% by weight of the aqueous mixture, from about 3% to about 8% by weight, or about 6% by weight.

The pH, temperature, concentration, mixing speed, or a combination thereof can be adjusted to form an aqueous mixture comprising a primary shell material, wherein the primary shell material comprises the first and second polymer components and surrounds the loading substance. If there is more than one type of polymer component (i.e., the first and second polymer components are different polymers), complex coacervation will occur between the components to form a coacervate, which further deposits around the loading substance to form primary shells of shell material. The pH adjustment depends on the type of shell material to be formed. For example, the pH may be adjusted to a value from about 3.5 to about 5.0, or from about 4.0 to about 5.0. If the pH of the mixture starts in the desired range, then little or no pH adjustment is required. In one example, the pH is adjusted to from about 3.5 to about 4.1, from about 3.6 to about 4.0, or from about 3.7 to about 3.9.

The initial temperature of the aqueous mixture can be from about 4° C. to about 60° C., or about 10° C. to about 50° C.

Mixing can be adjusted so that there is good mixing without breaking the microcapsules as they form. Particular mixing parameters depend on the type of equipment being used. Any of a variety of types of mixing equipment known in the art may be used. In one example, an axial flow impeller, such as LIGHTNIN™ A310 or A510, can be used.

In many examples disclosed herein, the primary shell and the outer shell of the disclosed microcapsules can comprise a complex coacervate. The complex coacervate can be formed from the first and second polymer components. For example, the primary shell and the outer shell can comprise a complex coacervate between whey protein isolate and agar. All combinations of first and second polymer components are contemplated herein for the complex coacervate and the primary and outer shell.

The aqueous mixture can then be cooled under controlled cooling rate and mixing parameters to permit agglomeration of the primary shells to form encapsulated agglomerations of primary shells. Not wishing to be bound by theory, the encapsulated agglomerations are discrete particles themselves. It is advantageous to control the formation of the encapsulated agglomerations at a temperature above the gel point of the shell material, and to let excess shell material form a thicker outer shell. It is also possible at this stage to add more polymer (e.g., a third polymer component), where the polymer is the same or different as the shell material being used, in order to thicken the outer shell and/or produce microcapsules having primary and outer shells of different composition. The outer shell encapsulates the agglomeration of primary shells to form a rigid encapsulated agglomeration of microcapsules.

Cooling the aqueous mixture can be accomplished by methods known in the art (e.g., the use of a chiller). The rate of cooling can be about 1° C. per about 1 to about 100 minutes. For example, the rate of cooling can be about 1° C. per about 1, 5, 10, 15, 20, 25, 30, 35, 40, 45, 50, 55, 60, 65, 70, 75, 80, 85, 90, 95, or 100 minutes, where any of the stated values can form an upper or lower endpoint when appropriate. In specific examples the rate of cooling can be about 1° C./5 minutes. Cooling can take place until the mixture reaches a temperature of from about 5° C. to about 10° C., e.g., about 5° C.

Processing aids can be included in the shell material (e.g., primary and/or outer shells). Processing aids can be used for a variety of reasons. For example, they may be used to promote agglomeration of the primary microcapsules, stabilize the emulsion system, improve the properties of the outer shells, control microcapsule size, and/or to act as an antioxidant. In one aspect, the processing aid can be an emulsifier, a fatty acid, a lipid, a wax, a microbial cell (e.g., yeast cell lines), a clay, or an inorganic compound (e.g., calcium carbonate). Not wishing to be bound by theory, these processing aids can improve the barrier properties of the microcapsules. In one aspect, one or more antioxidants can be added to the shell material. Antioxidant properties are useful both during the process (e.g., during coacervation and/or spray drying) and in the microcapsules after they are formed (i.e., to extend shelf-life, etc). Preferably a small number of processing aids that perform a large number of functions can be used. In one aspect, the antioxidant can be a phenolic compound, a plant extract, or a sulfur-containing amino acid. In one aspect, ascorbic acid or citric acid (or a salt thereof such as sodium or potassium ascorbate or sodium or potassium citrate) can be used to promote agglomeration of the primary microcapsules, to control microcapsule size and to act as an antioxidant. The antioxidant can be used in an amount of about 100 ppm to about 12,000 ppm, or from about 1,000 ppm to about 5,000 ppm. Other processing aids such as, for example, metal chelators, can be used as well. For example, ethylene diamine tetraacetic acid can be used to bind metal ions, which can reduce the catalytic oxidation of the loading substance.

In the disclosed microcapsules, the shell material can also be cross-linked. Thus, the disclosed methods can further involve the addition of a cross-linker. The cross-linker can be added to further increase the rigidity of the microcapsules by cross-linking the shell material in both the outer and primary shells and to make the shells insoluble in both aqueous and oily media. In one example, the cross-linker is added after the outer shell of the microcapsule is produced. Any suitable cross-linker can be used and the choice of cross-linker can vary depending upon the selection of the first and second polymer component. In another example, the cross-linkers can be enzymatic cross-linkers (e.g. transglutaminase), aldehydes (e.g. formaldehyde or glutaraldehyde), tannic acid, alum or a mixture thereof. In another aspect, the cross-linker can be a plant extract or a phenolic. It is also contemplated that one or more loading substances (e.g., antioxidants) can be used with the cross-linker. When the microcapsules are to be used in a formulation that is to be delivered to an organism, the cross-linkers are preferably non-toxic or of sufficiently low toxicity. The amount of cross-linker used depends on the components selected and can be adjusted to provide more or less structural rigidity as desired. In one aspect, the amount of cross-linker that can be used is in the amount of about 0.1% to about 5.0%, about 0.5% to about 5.0%, about 1.0% to about 5.0%, about 2.0% to about 4.0%, or about 2.5%, by weight of the first polymer component. In general, one skilled in the art can routinely determine the desired amount in any given case by simple experimentation. The cross-linker can be added at any stage of the process; however, it can typically be added after the cooling step.

Further, in some applications, the use of transglutaminase to crosslink the microcapsules may not be desired (e.g., the temperature and pH are too low and/or the transglutaminase is expensive). Thus, it is contemplated herein that the use of glutaraldehyde can be in the disclosed methods to cross-link the disclosed microcapsules. In certain examples, the use of one or more compositions comprising an amino acid or protein, can react with residual glutaraldehyde that was totally or partially unreacted from the crosslinking reaction. That is, unreacted and half reacted glutaraldehyde (i.e., with one aldehyde group still reactive) can be neutralized by the ∈-amino group of lysine or other amino groups on proteins, making the final product safer. In this sense, the compositions comprising amino acids and/or proteins can improve the microcapsule shell by filling any pores and neutralize glutaraldehyde from the crosslinking reaction. This approach can also eliminate the need to wash the microcapsule after crosslinking since the microcapsule will be essentially free of glutaraldehyde. Crosslinking can also be accomplished with genipin (e.g., with genipin and carboxylmethyl chitosan).

It is also possible to crosslink the disclosed microcapsules with heat. For example, heating to about 80° C. for 30 minutes or heating to 95° C. for 5 minutes can effectively crosslink the disclosed microcapsules.

Further, the disclosed microcapsules can be washed with water and/or dried to provide a free-flowing powder. Thus, the disclosed methods of preparing microcapsules can comprise a drying step for the microcapsules. Drying can be accomplished by a number of methods known in the art such as, for example, freeze drying, drying with ethanol, or spray drying. In one aspect, spray drying can be used for drying the microcapsules. Spray drying techniques are disclosed in "Spray Drying Handbook", K. Masters, 5th edition, Longman Scientific Technical UK, 1991, the disclosure of which is hereby incorporated by reference at least for its teaching of spray drying methods.

Incorporating Drying/Anticaking Agents to Improve Powder Flowability

Drying agents or anticaking agents can be used to help produce free flowing powders. Typically, drying agents have high porosity, which can help adsorb surface oil and flavor compounds due to the raw materials, or the oxidation of lipids. Examples of suitable drying and/or anticaking agents include, but are not limited to, HUBERSORB™ and ZEOTHIX™ (J. M. Huber Corp; Harve de Grace, Md.) and CAPSUL™ (from National Starch & Chemical Co.) and VITACEL™ (J. Rettenmair USA; Schoolcraft, Mich.).

Incorporating Antioxidants into the Powder

In other examples, disclosed herein are methods for incorporating antioxidants into and/or onto the primary shell, the outer shell(s), or both primary and outer shell(s). materials. The disclosed methods comprise providing a microcapsule as disclosed herein, providing an emulsion comprising a polymer component and an antioxidant; combining the emulsion and the microcapsule, to thereby provide a microcapsule with a shell material comprising the antioxidant. The resulting suspension can then be cooled and the coated microcapsules can be dried. In many suitable examples, the microcapsules can be included in a slurry that contains the antioxidants and the slurry can be spray dried. Suitable antioxidants include, but are not limited to, CoQ10, lutein, zeaxanthan, carotene, and combinations thereof. These can be used alone or in addition to the amino acids, proteins, saccharides, or waxes disclosed herein.

Formulation Vehicles

Also disclosed herein are formulation vehicles comprising the microcapsules disclosed herein. Any of the microcapsules described herein can be incorporated into a formulation vehicle. Examples of formulation vehicles are provided herein and include, but are not limited to, foodstuffs, beverages, nutraceutical formulations, pharmaceutical formulations, lotions, creams, or sprays. In some other specific examples, the disclosed emulsions and/or microcapsules can be incorporated into gels, gel capsules, or tablets. Other vehicles include powders or powders coated with a polymer. Such vehicles can be given orally or, in the case of powders for example, sprinkled onto food or beverages.

Supplements

Also, disclosed herein are nutritional supplements that comprise the microcapsules disclosed herein. A nutritional supplement is any compound or composition that can be administered to or taken by a subject to provide, supply, or increase a nutrient(s) (e.g., vitamin, mineral, essential trace element, amino acid, peptide, nucleic acid, oligonucleotide, lipid, cholesterol, steroid, carbohydrate, and the like). For example, a nutritional supplement can comprise a composition comprising one or more loading substances disclosed herein.

The nutritional supplement can comprise any amount of the microcapsules disclosed herein, but will typically contain an amount determined to supply a subject with a desired dose of a loading substance (e.g., EPA and/or DHA). The exact amount of microcapsules required in the nutritional supplement will vary from subject to subject, depending on the species, age, weight and general condition of the subject, the severity of any dietary deficiency being treated, the particular mode of administration, and the like. Thus, it is not possible to specify an exact amount for every nutritional supplement. However, an appropriate amount can be determined by one of ordinary skill in the art using only routine experimentation given the teachings herein.

The nutritional supplement can also comprise other nutrient(s) such as vitamins other trace elements, minerals, and the like. Further, the nutritional supplement can comprise other components such as preservatives, antimicrobials, anti-oxidants, chelating agents, thickeners, flavorings, diluents, emulsifiers, dispersing aids, or binders.

The nutritional supplements are generally taken orally and can be in any form suitable for oral administration. For example, a nutritional supplement can typically be in a tablet, gel-cap, capsule, liquid, sachets, or syrup form.

The nutritional supplements can be designed for humans or animals, based on the recommended dietary intake for a given individual. Such considerations are generally based on various factors such as species, age, and sex as described above, which are known or can be determined by one of skill in the art. In one example, the disclosed supplements can be used as a component of feed for animals such as, but not limited to, livestock (e.g., pigs, chickens, cows, goats, horses, and the like) and domestic pets (e.g., cats, dogs, birds, and the like).

Pharmaceutical Formulations

Also, pharmaceutical formulations comprising the disclosed microcapsules are disclosed herein. A suitable pharmaceutical formulation can comprise any of the disclosed compositions with a pharmaceutically acceptable carrier. For example, a pharmaceutical formulation can comprise one or more of the disclosed microcapsules and a pharmaceutically acceptable carrier. The disclosed pharmaceutical formulations can be used therapeutically or prophylactically.

By "pharmaceutically acceptable" is meant a material that is not biologically or otherwise undesirable, i.e., the material can be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, 21$^{st}$ ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like can be desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids, or binders can be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Foodstuffs

Also disclosed herein are foodstuffs that comprise any of the disclosed microcapsules. By "foodstuff" is meant any article that can be consumed (e.g., eaten, drank, or ingested) by a subject. In one example, the disclosed compositions can be used as nutritional supplements that are added to a foodstuff. For example, the disclosed microcapsules can be added to food or beverages. In this sense, the disclosed compositions can be prepared in, for example, a powdered form and contained in articles such as sachets or shakers, which can be used to pour or sprinkle the disclosed compositions onto and into food and beverages.

In some examples, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In other examples, the foodstuff is bread, tortillas, cereal, sausage, chicken, ice cream, yogurt, milk, salad dressing, rice bran, fruit juice, a dry beverage powder, liquid beverage, rolls, cookies, crackers, fruit pies, or cakes.

Methods of Use

The disclosed microcapsules also have a wide variety of uses. For example, disclosed herein are methods of delivering a loading substance to a subject by administering to the subject a microcapsule as disclosed herein. Also disclosed is the use a microcapsule as disclosed herein to prepare a medicament for delivering a loading substance to a subject. The disclosed microcapsules can be particularly useful for delivering substances to those on vegan, lactovegetarian, ovo-lactovegetarian, and/or semi-vegetarian diets.

The use of microcapsules can protect certain compositions from oxidation and degradation, keeping the loading substance fresh. Also, because microcapsules can hide the unpleasant odor or taste of certain compositions, the methods disclosed herein can be particularly useful for delivering and supplementing unpleasant compositions. Still further, the use of microcapsules can allow various loading substances to be added to food articles which are otherwise not amenable to supplementation. For example, omega-3 fatty acids can degrade or oxidize in air and can be sensitive to food preparation techniques (e.g., baking). By the use of microencapsulated omega-3 fatty acids, these compositions can be added to food without significant degradation during food preparation.

Particularly suitable microcapsules include those that are resistant to rupture during the preparation of the food article (including packaging, transportation, and storage of the food article). In some examples, the microcapsules can be of a size and consistency that does not detract from the texture and constitution of the food article.

In a particular example, the disclosed microcapsules (including nutritional supplements, pharmaceutical formulations, delivery devices, and foodstuffs that contain the disclosed microcapsules) can be used as a source of fatty acids (e.g., omega-3 fatty acids), lowering triglycerides and influencing diabetes related biochemistry. In another particular example, disclosed herein are methods of supplementing omega-3 fatty acids in a subject by administering an effective amount of a microcapsule disclosed herein, wherein the loading substance comprises an omega-3 fatty acid. In another example, disclosed herein are methods of lowering cholesterol levels, triglyceride levels, or a combination thereof in a subject by administering an effective amount of an emulsion and/or microcapsule disclosed herein.

Omega-3 fatty acids are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are well established. These compounds are also known for other cardioprotective benefits such as preventing cardiac arrhythmias, stabilizing atherosclerotic plaques, reducing platelet aggregation, and reducing blood pressure. See e.g., Dyrberg et al., In: Omega-3 Fatty Acids Prevention and Treatment of Vascular Disease. Kristensen et al., eds., Bi & Gi Publ., Verona-Springer-Verlag, London, pp. 217-26, 1995; O'Keefe and Harris, *Am. J. Cardiology* 2000, 85:1239-41; Radack et al., "The effects of low doses of omega-3 fatty acid supplementation on blood pressure in hypertensive subjects: a randomized controlled trial." *Arch. Intern. Med.* 1991, 151:1173-80; Harris, "Extending the cardiovascular benefits of omega-3 fatty acids." *Curr. Atherosder. Rep.* 2005, 7:375-80; Holub, "Clinical nutrition: 4 omega-3 fatty acids in cardiovascular care." *CMAJ* 2002, 166(5):608-15. Indeed, the American Heart Association has also reported that omega-3 fatty acids can reduce cardiovascular and heart disease risk. Other benefits of omega-3 fatty acids are those related to the prevention and/or treatment of inflammation and neurodegenerative diseases, and to improved cognitive development. See e.g., Sugano and Michihiro, "Balanced intake of polyunsaturated fatty acids for health benefits." *J. Oleo Sci.* 2001, 50(5):305-11.

The fatty acids EPA and DHA can be synthesized in the human body from α-linolenic acid (18:3); however, the conversion rate from this precursor molecule is limited (Muskiet et al., "Is docosahexaenoic acid (DHA) essential? Lessons from DHA status regulation, our ancient diet, epidemiology and randomized controlled trials." *J. Nutr.* 2004, 134(1):183-6). Accordingly, EPA and DHA in the body are primarily derived from dietary sources (e.g., oily fish). Diets rich in fish oils are known to have many beneficial effects for heart disease, cancer, arthritis, allergies, and other chronic diseases. Epidemiological clinical trials have shown that increasing the dietary intake of omega-3 fatty acids, in the form of fish or of fish oil supplements, may reduce various risk factors associated with cardiovascular disease. See e.g., The American Heart Association, Scientific Statement, "Fish Consumption, Fish Oil, Omega-3 Fatty Acids and Cardiovascular Disease," November 2002; Appel et al., "Does supplementation of diet with 'fish oil' reduce blood pressure? A meta-analysis of controlled clinical trials." *Arch. Intern. Med.* 1993, 153(12):1429-1438; GISSI-Prevenzione Investigators. "Dietary supplementation with omega-3 polyunsaturated fatty acids and vitamin E after myocardial infarction: results of the GISSI-Prevenzione trial." *Lancet* 1999, 354:447-55.

Despite the strong evidence for the benefit of omega-3 fatty acids like EPA and DHA in prevention of cardiovascular disease, the average daily consumption of these fatty acids by North Americans is estimated to be between 0.1 to 0.2 grams, compared to a suggested daily intake of 0.65 grams to confer benefit (Webb, "Alternative sources of omega-3 fatty acids." *Natural Foods Merchandiser* 2005, XXVI(8):40-4). Since altering dietary patterns of populations is difficult and many people do not like to eat fish, dietary supplementation with EPA and DHA is an important approach to addressing this problem. Unfortunately, many supplements of omega-3 fatty acids are sensitive to oxidation and can be foul smelling and tasting. Further, compliance with dietary supplement regimens requires discipline, which is often wanting. In light of the health benefits of omega-3 fatty acids, the disclosed microcapsules can be used to deliver omega-3 fatty acids to a subject.

In the disclosed methods of use, the emulsions and/or microcapsules that are administered can be any of the compositions disclosed herein. For example, the disclosed microcapsules can be used in the disclosed methods in the form of any of the nutritional supplements disclosed herein. In another example, the disclosed microcapsules can be used in the disclosed methods in the form of any of the pharmaceutical formulations disclosed herein. In still another example, the disclosed microcapsules can be incorporated in any of the delivery devices disclosed herein, or incorporated into any foodstuff disclosed herein and used in the disclosed methods.

It is contemplated that the methods disclosed herein can be accomplished by administering various forms of the disclosed microcapsules. For example, one can administer any of the pharmaceutical formulations with any of the foodstuffs disclosed herein. In another example, one can administer a tablet or capsule with any of the nutritional supplements disclosed herein. In yet another example, one can administer any of the pharmaceutical formulations with any of the delivery devices and nutritional supplement disclosed herein, and the like.

Dosage

When used in the above described methods or other treatments, or in the nutritional supplements, pharmaceutical formulations, delivery devices, or foodstuffs disclosed herein, an "effective amount" of one of the disclosed microcapsules can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

Further, disclosed are methods for delivering a disclosed composition to a subject by administering to the subject any of the nutritional supplements, pharmaceutical formulations, delivery devices, and/or foodstuffs disclosed herein. The disclosed compositions (including nutritional supplements, delivery devices, and pharmaceutical formulations) can typically be administered orally.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada, Ltd. (Dartmouth, NS, Canada), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplements (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1: Microencapsulation Using WPI/Agar-WPI/Gellan Gum 4.0 g of agar (TIC pretested agar; TIC Gums; Belcamp, Md.) was added to 100.0 g of boiling water to be hydrated and dissolved. The resulting solution was then transferred into a 2-L reactor with 600.0 g of deionized water maintained at 65° C. Next, 1.0 g of sodium ascorbate was added to the solution in the reactor and the pH was determined to be about 6.6.

35.0 g of WPI (whey protein isolate) (Alacen® 895, NZMP (USA) Inc., Lemoyne, Pa.) was added to 90.0 g of deionized water under agitation at room temperature (25° C.). The dissolved WPI was then cooled to 10° C. 70.0 g of fish oil (XODHA from Ocean Nutrition Canada, Ltd.; Dartmouth, NS) was added to the cold WPI solution and the resulting mixture was emulsified by a POLYTRON PT 6100™ homogenizer (Kinematica AG, Lucerne, Switzerland) at 8000 rpm for 5 minutes while the temperature was maintained at 10° C. The resulting emulsion was examined under a microscope after emulsification to verify that the oil droplets were small and uniform (about 1-5 µm in diameter).

The emulsion was added to the agar solution in the reactor. The pH value of the resulting mixture was about 6.4. Then, pH was adjusted to about 5.0 with 10% w/w phosphoric acid to form about 30 µM agglomerations of primary microcapsules.

4.0 g of low acyl gellan gum (Kelcogel F, from CPKELCO; San Diego, Calif.) and 4.0 g of WPI were dissolved in 600.0 g of deionized water at about 60° C. The solution pH, which was initially 6.2, was adjusted to 5.0 with 10% w/w phosphoric acid. This mixture was added to the microcapsules in the reactor. 3.0 g of $CaCl_2$ in 20.0 g of distilled water solution was prepared and also added to the suspension of microcapsules. The resulting slurry was quickly cooled to 20° C. and agitation speed was increased during cooling to avoid gelling. The finished suspension of microcapsules was ready for spray drying to produce a free flowing powder. Such a microcapsule would be suitable for a lactovegetarian, ovo-lactovegetarian, and semi-vegetarian diet.

Example 2: Microencapsulation Using Whey Protein and Low Methoxyl Pectin 29.3 g of whey protein isolate (WPI, Alacen 895, NZMP (USA) Inc.) was dissolved in 322 g of water in a 2-L reactor with agitation. The resulting solution was kept at 30° C. while 7 g of sodium ascorbate was then added. 15 g of fish oil (XO30TG, Ocean Nutrition Canada, Ltd.) was next added to the WPI solution. The solution was then emulsified with a POLYTRON PT 6100™ homogenizer at 10,000 rpm for 5 minutes. Next, 972 g of distilled water was added to the resulting emulsion in the reactor while the temperature was maintained at 30° C. 14.6 g of pretested PECTIN LM32™ from TIC Gums (Belcamp, Md.) were dissolved in 168.2 g of distilled water and then added to the diluted emulsion in the reactor. Suspension pH was adjusted to 3.1 with 10% phosphoric acid (about 50 mL) to form about 10 μm agglomerations of primary microcapsules. The mixture was then heated from 30° C. to 85° C. at an average heating rate of 1.3° C. per minute. The particle size increased to 30 μm and the mixture was cooled to room temperature naturally and agitated overnight. The finished suspension of microcapsules was then ready for coating processes, or spray dried to produce a free flowing powder. Such a microcapsule would be suitable for a lactovegetarian, ovo-lactovegetarian, and semi-vegetarian diet.

Example 3: Microencapsulation Using Gelatin and Low Methoxyl Pectin 570 g of deionized water was added to a reactor and heated to about 53° C. 8.0 g of low methoxyl pectin (LM-12 CG™ from C.P. Kelco; San Diego, Calif.) was dissolved in 349 g of water at about 53° C. 40.0 g of fish gelatin (240 Bloom, from LAPI; Tuscany, Italy) was dissolved in 293 g of water at about 53° C. After the gelatin was completely dissolved, 6.1 g of sodium ascorbate was added to the gelatin solution. 72.0 g of DHA oil (XODHA, Ocean Nutrition Canada, Ltd.) was then added to the gelatin solution and the resulting mixture was emulsified with a POLYTRON PT 6100 homogenizer at 7500 rpm for 4 minutes. The emulsion was then added to water in the reactor and pH of the solution was adjusted to 8.04. The pectin solution was then added to the reactor and coacervation was commenced with the addition of citric acid until pH 4.52 and the desired particle size was reached (about 30 μm). The slurry was cooled at 5° C. per minute to 4° C. Once the slurry reached 4° C., 2.6 g of transglutaminase (ACTIVA TI, Ajinomoto Co. Inc., Tokyo, JP) was added and pH was adjusted to 5.04. Temperature was then raised to 25° C. in 30 minutes and maintained for crosslinking at 25° C. for 12 hours. The slurry of microcapsules was then ready for use in food or spray drying to produce a free flowing powder. Such a microcapsule would be suitable for a semi-vegetarian diet.

Example 4: Microencapsulation Using Gelatin-Alginate (One-Step Process)

44.8 g of fish gelatin (240 Bloom, LAPI) was dissolved in 254 g of water. This solution was then heated to 40° C. 1179 g of distilled water was added to a 2-L reactor and temperature was maintained at 40° C. An amount of 7.5 g ascorbic acid was added into the reactor. Next, 30 mL of 10% citric acid were added to the reactor. The solution pH was 3.3. An amount of 10% NaOH solution was then added to the reactor to reach a pH of 4.8.

72.0 g of fish oil (XO30TG, Ocean Nutrition Canada, Ltd.) was added to the gelatin solution. The resulting solution was then emulsified with a POLYTRON PT 6100™ homogenizer at 7500 rpm for 4 minutes. The resulting emulsion was examined under a microscope after emulsification to verify that the oil droplets were small and uniform (about 1-5 μm in diameter).

The emulsion was added to distilled water in the reactor and pH of the mixture was found be 4.9. NaOH was then added to bring the pH to 5.4.

3.2 g of alginate (PROTANAL LFR 5/60™ from FMC Biopolymer; Philadelphia, Pa.) was dissolved in 61 g of distilled water. This alginate solution was then added to the diluted emulsion in the reactor. The mixture in the reactor had a pH of 5.5 and the oil droplets were 1-3 μm in diameter. Suspension pH was then lowered with 10% citric acid in order to form agglomerations of primary microcapsules. After pH was lowered to 5.0 with the addition of 12 mL of acid, the slurry was cooled to 4° C. with controlled cooling at 5° C. per minute.

3.1 g of transglutaminase dissolved in 10 g of distilled water were added to the microcapsules at 4° C. Temperature was raised to 25° C. in 30 minutes for crosslinking overnight (12 hours). The finished suspension of microcapsules was then ready for food processes, or spray dried to produce a free flowing powder. Such a microcapsule would be suitable for a semi-vegetarian diet.

Example 5: Microencapsulation Using Gelatin-Alginate (Two-Step Process)

22.6 g of fish gelatin (240 Bloom, LAPI) was dissolved in 160 g of water. 7.6 g of sodium ascorbate was then added and the solution was heated to 40° C. The solution pH was adjusted to 6.0 by adding 10% NaOH solution.

1.4 g of alginate (PROTANAL LFR 5/60™, FMC Biopolymer) was dissolved in 44 g of distilled water. This alginate solution was then added to the gelatin solution.

569 g of distilled water was added to a 2-L reactor and the temperature was maintained at 40° C. 69.0 g of fish oil (XO30TG, Ocean Nutrition Canada, Ltd.) was added to the gelatin and alginate solution and then emulsified with a POLYTRON PT 6100™ homogenizer at 7500 rpm for 3 minutes. The emulsion was examined under a microscope after emulsification and verified that the oil droplets were small and uniform (about 1-5 μm in diameter). The emulsion was added to distilled water in the reactor and the pH value of the mixture was 5.8. The pH value was then lowered with 10% citric acid in order to form agglomerations of primary microcapsules. After pH was lowered to 5.1 with the addition of 4.5 mL of acid, the slurry was cooled to 37° C.

A gelatin solution and an alginate solution were prepared for the second step process as follows. 18.6 g of fish gelatin (LAPI) was dissolved in 251 g of water with 3.0 g of sodium ascorbate. This solution was then heated to 37° C. 2.3 g of alginate was dissolved in 384 g of distilled water. The resulting alginate solution was then heated to 37° C. and mixed with the gelatin solution. The mixture was cloudy and had a pH of 5.1. A 10% NaOH solution was added to the mixture to bring the pH up to 5.6. The solution became at least partially transparent. The mixture was added to the slurry of microcapsules in the reactor with increased agitation to prevent clumping. The slurry was cooled at 5° C. per minute to 4° C.

3.1 g of transglutaminase dissolved in 10 g of distilled water was added to the slurry at 4° C. Temperature was then increased to 25° C. for crosslinking overnight (12 hours). The finished suspension of microcapsules was then ready for food processes, or spray dried to produce a free flowing powder. Such a microcapsule would be suitable for a semi-vegetarian diet.

Example 6: Microencapsulation Using SPI/Agar-SPI/Gellan Gum 4.0 g of agar was added to 100.0 g of boiling water to be hydrated thoroughly. The solution was then transferred into a 2-L reactor with 600.0 g of distilled water maintained at 65° C.

45.0 g of soy protein isolate (SPI) (ICN Biomedicals, Inc.; Irving, Calif.) was added to 300.0 g of distilled water under agitation and warmed to 65° C. to dissolve. 60.0 g of fish oil (XODHA, Ocean Nutrition Canada, Ltd.) was added to the SPI solution. The resulting mixture was then emulsified with a POLYTRON PT 6100 homogenizer at 8000 rpm for 8 minutes. The emulsion was examined under a microscope after emulsification to verify that the oil droplets were about 5 μm in diameter. The emulsion was then added to the agar solution in the reactor and the pH of the mixture was about 6.7. The pH was adjusted to 5.0 with 10% w/w phosphoric acid to form about 30 μm agglomerations of primary microcapsules.

4.0 g of low acyl gellan gum and 8.0 g of SPI were dissolved in 400.0 g of distilled water at about 60° C. The pH was adjusted from 6.6 to 5.0 with 10% w/w phosphoric acid. The resulting mixture was added to the suspension of microcapsules in the reactor. 1.5 g of $CaCl_2$ in 10.0 g of distilled water was then added to the reactor. The resulting slurry was then quickly cooled to 20° C. and agitation speed was increased during cooling to avoid gelling. The finished suspension of microcapsules was ready for spray drying to produce a free flowing powder. Such a microcapsule would be suitable for a vegan, lactovegetarian, ovo-lactovegetarian, and semi-vegetarian diet.

Example 7: Microencapsulation Using SPI/Agar/Gellan Gum with ARA Oil 40.0 g soy protein isolate (ICN Biomedicals, Inc.) was dissolved in 330.0 g of distilled water. The resulting solution was heated up to 60° C. and pH was adjusted to about 11.

60.0 g of ARA oil (Wuhan Fuxing Biotechnology Pharmaceutical Co. Ltd., Wuhan, China) was heated to 50° C. The ARA oil was then added to the soy protein solution and emulsified at 8000 rpm for 5 minutes. The emulsion was examined under a microscope after emulsification to verify that the oil droplets were about 1-2 μm in diameter.

3.0 g of agar (TIC pretested agar, TIC Gums; Belcamp, Md.) was dissolved in 100.0 g of boiling distilled water and then transferred to a 2-L reactor with 600.0 g distilled water and 5.0 g of sodium ascorbate. Temperature was maintained at 55° C. and the mixture had a pH of about 7.0.

The emulsion was then added to the reactor and the pH of the mixture was about 10.8. The pH value was then adjusted to about 5.7 with 10% phosphoric acid to form about 40 μm agglomerations of the primary microcapsules.

3.2 g of transglutaminase in 10.0 g of distilled water was added to the reactor and the suspension was maintained at 50° C. for 3 hours before being cooled down to 44° C. 5.0 g of gellan gum (Kelcogel F, CPKELCO) and 2.0 g of sodium ascorbate were dissolved in 400.0 g of distilled water at 65° C. and then cooled to 50° C. 4.0 g of SPI was dissolved in 50.0 g of distilled water with pH adjusted to about 9. The SPI solution was then mixed with the gellan gum solution and the pH value was adjusted to about 6.7. The resulting SPI/gellan gum solution was then added to the agglomerated primary microcapsules in the reactor at 44° C.

1.60 g $CaCl_2$ in 10.0 g distilled water was added to the reactor and agitation speed was increased gradually as the solution was quickly cooled down to 20° C. The finished suspension of microcapsules had a compact structure and shell, and the shell survived after boiling. Such a microcapsule would be suitable for a vegan, lactovegetarian, ovo-lactovegetarian, and semi-vegetarian diet.

Example 8: Microencapsulation Using SPI/Agar/Gellan Gum with Algal Oil 26.67 g of soy protein isolates (ICN Biomedicals, Inc.) was dissolved in 220.0 g of distilled water. The resulting solution was heated up to 60° C. and the pH was adjusted to 10.6.

40.0 g of algal oil (DHASCO-S from Martek Biosciences; Columbia, Md.) was heated to 50° C. The algal oil was then added to the soy protein solution and emulsified at 8000 rpm for 5 minutes. The emulsion was examined under a microscope after emulsification to verify that the oil droplets were about 1 μm in diameter.

2.0 g of agar (TIC pretested agar, TIC Gums; Belcamp, Md.) was dissolved in 66.7.0 of boiling distilled water and then transferred to a 2-L reactor with 400.0 g of distilled water and 3.33 g of sodium ascorbate. The temperature in the reactor was maintained at 55° C. and the mixture had a pH of about 7.0.

The algal oil emulsion was added to the distilled water in the reactor and the pH of the mixture was about 10.2. The pH was then adjusted to about 5.7 with 10% w/w phosphoric acid to form about 30 μm agglomerations of the primary microcapsules.

2.1 g of transglutaminase in 10.0 g of distilled water was next added to the reactor and the mixture was maintained at 50° C. for 3 hours before cooling down to 44° C.

2.67 g of gellan gum (Kelcogel F) and 1.33 g of sodium ascorbate were dissolved in 266.7 g of distilled water at 65° C. and then cooled to 50° C. 2.6 g of SPI was dissolved in 30.0 g of distilled water with pH adjusted to about 9. The SPI solution was then mixed with the gellan gum solution and pH was adjusted to about 6.7. The resulting SPI/gellan gum solution was then added to the agglomerated primary microcapsules in the reactor at 44° C.

1.0 g of $CaCl_2$ in 5.0 g distilled water was added to the reactor and the agitation speed was gradually increased as the solution was quickly cooled down to 20° C. The finished suspension of microcapsules had a compact structure and shell, and the shell survived after boiling. Such a microcapsule would be suitable for a vegan, lactovegetarian, ovo-lactovegetarian, and semi-vegetarian diet.

Example 9: Microencapsulation Using SPI/Agar/Gellan Gum with Omega-3 Oil 8.9 g of soy protein isolates (ICN Biomedicals, Inc.) was dissolved in 73.3 g of distilled water. The resulting solution was heated to 60° C. and pH was adjusted to 10.6.

13.3 g of omega-3 oil (ONC-T18, Ocean Nutrition Canada Ltd.) was heated to 70° C. and then added to the soy protein solution and emulsified at 8000 rpm for 5 minutes. The emulsion was examined under a microscope after emulsification to verify that the oil droplets were about 1-2 µm in diameter.

0.67 g of agar (TIC pretested agar, TIC Gums; Belcamp, Md.) was dissolved in 22.2 g of boiling distilled water and transferred to a 500 mL reactor with 133.3 g of distilled water and 1.11 g of sodium ascorbate. Temperature was maintained at 55° C. and the mixture had a pH of about 7.0. The omega-3 oil emulsion was then added to the reactor and pH of the mixture was found to be about 10.8. The pH value was then adjusted to about 5.7 with 10% phosphoric acid to form about 30 µm agglomerations of the primary microcapsules.

0.71 g of transglutaminase in 5.0 g of distilled water was added to the reactor and the temperature was maintain at 50° C. for 3 hours before being cooled down to 44° C.

0.89 g of gellan gum (Kelcogel F, CPKELCO) and 0.44 g of sodium ascorbate were dissolved in 89.0 g of distilled water at 65° C. and then cooled to 50° C. 0.89 g of SPI was dissolved in 10.0 g of distilled water at apH of about 9. The SPI solution was mixed with the gellan gum solution and pH was adjusted to about 6.7. The SPI/gellan gum solution was then added to the agglomerated primary microcapsules in the reactor at 44° C.

0.33 g of $CaCl_2$ in 3.0 g of distilled water was added to the reactor, and the agitation speed was gradually increased as the mixture was quickly cooled down to 20° C. The finished suspension of microcapsules had a compact structure and shell, and the shell did not change after boiling. Such a microcapsule would be suitable for a vegan, lactovegetarian, ovo-lactovegetarian, and a semi-vegetarian diet.

Example 10: Microencapsulation Using WPI/Gum Arabic 30.0 g of WPI (whey protein isolate) (ALACEN™ 895, NZMP (USA) Inc., Lemoyne, Pa.) and 15.0 g of gum arabic (TIC Gums; Belcamp, Md.) were dissolved in 130.0 g of distilled water under agitation at room temperature (25° C.).

67.0 g of fish oil (XODHA from Ocean Nutrition Canada, Ltd.; Dartmouth, NS) was heated to 50° C. to be melted and then added to the WPI solution. The resulting mixture was cooled to 10° C. and emulsified by a POLYTRON PT 6100™ homogenizer (Kinematica AG, Lucerne, Switzerland) at 8000 rpm for 5 minutes while the temperature was maintained at 10° C. The resulting emulsion was examined under a microscope after emulsification to verify that the oil droplets were small and uniform (about 1-2 µm in diameter).

The emulsion was added to a 1.5 L reactor with 1200.0 g distilled water and 6.7 g sodium ascorbate at room temperature. The pH value of the resulting mixture was about 6.4. pH was then adjusted to about 3.9 with 10% w/w phosphoric acid to form about 30 µm agglomerations of primary microcapsules.

The resulting suspension was heated up to 95° C. and held for 5 minutes, then cooled to room temperature. The finished suspension of microcapsules was spray dried to produce a free flowing powder with a compact structure. The induction period was greater than 90 hours at 65° C. Such a microcapsule would be suitable for a lactovegetarian, ovo-lactovegetarian, and semi-vegetarian diet.

This example was also performed where a solation of fish oil and WPI were first emulsified and then the gum arabic was added. It was found, however, that more compact coacervates could be obtained by emulsifying fish oil with both WPI and gum arabic. Further, a higher pH endpoint was used (4.2). But at 3.9 it was found that more compact microcapsules could be obtained. Also, the induction period of microcapsules made with a pH endpoint of 3.9 was much longer than those made with a pH endpoint of 4.2 (90 hours at 65° C. versus 30 hours). Moreover, heat (80° C. for 30 minute) and enzyme crosslinking were used. It was found, however, that a single heat crosslinking at 95° C. for 5 minutes generated better sensory qualities for the microcapsules.

Example 11: Microencapsulation Using SPI-Sodium Caseinate 40.0 g of SPI (ICN Biomedicals, Inc.) was dissolved in 350.0 g of distilled water at 50° C. and the pH was adjusted to 9. Then, 75.0 g of fish oil (Ocean Nutrition Canada) was heated to 50° C. to be melted, and then added to the SPI solution. The resultant solution was then emulsified at 9300 rpm for 5 minutes. The emulsion was examined under a microscope after emulsification to verify that the oil droplets were small (around 2 µm in diameter).

10.0 g sodium casinate (NZMP ALANATE 180) was dissolved in a 1.5 L reactor with 800.0 g of distilled water and 6.3 g of sodium ascorbate at room temperature, the solution in the reactor had a pH around 6. The emulsion of SPI and fish oil was added to the sodium caseinate solution in the reactor and the pH of the mixture was around 9.

pH was then adjusted to about 5.0 with 20% w/w phosphoric acid to form about 40 µm agglomerations of the primary microcapsules. The suspension was heated to 95° C. and held for 10 minutes, then cooled down to room temperature.

The finished suspension of microcapsules with compact structure, and round particles was provided after spray-dry. Such a microcapsule would be suitable for a lactovegetarian, ovo-lactovegetarian, and semi-vegetarian diet.

Example 12: Microencapsulation Using Pea Protein Isolates-Sodium Caseinate 40.0 g of pea protein isolates (PPI) (Nutri-Pea Limited; Manitobe, Canada) was dissolved in 180.0 g of distilled water at room temperature. 75.0 g of fish oil (Ocean Nutrition Canada) was heated to 50° C. to be melted, and then added to the PPI solution. The solution was then emulsified at 9300 rpm for 4 minutes. The emulsion was examined under a microscope after emulsification to verify that the oil droplets were small (around 4 µm in diameter).

10.0 g of sodium caseinate (NZMP ALANATE 180) was dissolved in a 1.5 L reactor with 957.0 g of distilled water and 6.3 g of sodium ascorbate at room temperature. The solution in the reactor had a pH around 6.4. The PPI and fish oil emulsion was added to the sodium caseinate solution in the reactor and the pH of the mixture was around 6.4.

pH was then adjusted to about 5.0 with 20% w/w phosphoric acid to form about 30 µm agglomerations of the primary microcapsules. The suspension was heated up to 95° C. and held for 10 minutes, then cooled down to room temperature.

The finished suspension of microcapsules with compact structure and round particles was provided after spray-dry. Such a microcapsule would be suitable for a lactovegetarian, ovo-lactovegetarian, and semi-vegetarian diet.

Example 13: Microencapsulation Using WPI-Sodium Caseinate 40.0 g WPI (Davisco, Bipro) and 10.0 g of sodium caseinate (NZMP ALANATE 180) were dissolved in 140.0 g of distilled water at room temperature. 75.0 g of fish oil (Ocean Nutrition Canada) was heated to 50° C. to be melted and then added to the above mixture. The resultant mixture was then emulsified at 9300 rpm for 5 minutes at 6° C. The emulsion was examined under a microscope after emulsification to verify that the oil droplets were small (around 2 μm in diameter).

5.3 g of sodium ascorbate was dissolved in a 1.5 L reactor with 800.0 g of distilled water at room temperature. The solution in the reactor had a pH around 7.4. Then the WPI-sodium caseinate-fish oil emulsion was added to the sodium ascorbate solution in the reactor and the pH of the mixture was around 6.5.

pH was then adjusted to about 4.7 with 20% w/w phosphoric acid to form about 30 μM agglomerations of the primary microcapsules. The suspension was heated to 90° C. and held for 20 minutes, then cooled down to room temperature.

The finished suspension of microcapsules with compact structure, and free flowing powder was provided after spray-dry. Such a microcapsule would be suitable for a lactovegetarian, ovo-lactovegetarian, and semi-vegetarian diet.

Example 14: Microencapsulation Using Gelatin-Sodium Caseinate 40.0 g pork gelatin (Nitta) and 10.0 g of sodium caseinate (NZMP ALANATE 180) were dissolved in 293.0 g distilled water at 50° C. 75.0 g of fish oil (Ocean Nutrition Canada) was heated to 50° C. to be melted and was then added to the gelatin solution. The mixture was then emulsified at 9000 rpm for 4 minutes. The emulsion was examined under a microscope after emulsification to verify that the oil droplets were small (around 1.3 μm in diameter).

In a 1.5 L reactor with 800.0 g distilled water, 6.3 g sodium ascorbate was added and the temperature was maintained at 45° C. The solution in the reactor had a pH around 6.4. The gelatin-fish oil emulsion was then added to the sodium ascorbate solution in the reactor and the pH of the mixture was around 5.8.

pH was then adjusted to about 4.7 with 20% w/w phosphoric acid to form about 20 μm agglomerations of the primary microcapsules. Complex coacervates were provided. Such a microcapsule would be suitable for a lactovegetarian, ovo-lactovegetarian, and semi-vegetarian diet.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A microcapsule, comprising: an agglomeration of primary microcapsules and a loading substance, each individual primary microcapsule having a primary shell, wherein the loading substance is encapsulated by the primary shell, wherein the agglomeration is encapsulated by an outer shell, and wherein the primary shell and the outer shell both comprise a complex coacervate of a first protein and a second polymer,
wherein the first protein is pea protein or soy protein;
and the second polymer is selected from the group consisting of agar, gellan gum, gum arabic, casein, cereal prolamine, pectin, alginate, carrageenan, xanthan gum, canola protein, dilutan gum, locus bean gum, and welan gum; and
wherein the primary and outer shells are thermally cross-linked.

2. The microcapsule according to claim 1, wherein the first protein comprises pea protein.

3. The microcapsule according to claim 1, wherein the primary and outer shells comprise a complex coacervate of pea protein isolate and casein.

4. The microcapsule according to claim 1, wherein the loading substance comprises microbial oil, fungal oil or a plant oil.

5. The microcapsule according to claim 1, wherein the loading substance comprises marine oil.

6. The microcapsule according to claim 1, wherein the loading substance comprises algal oil.

7. The microcapsule according to of claim 1, wherein the loading substance comprises fish oil.

8. The microcapsule according to claim 1, wherein the loading substance comprises an omega-3 fatty acid, an alkyl ester of an omega-3 fatty acid, a triglyceride ester of an omega-3 fatty acid, a phytosterol ester of an omega-3 fatty acid, arachidonic acid, and/or a mixture thereof.

9. The microcapsule according to claim 1, wherein the loading substance comprises docosahexaenoic acid and/or eicosapentaenoic acid, a $C_1$-$C_6$ alkyl ester thereof, a triglyceride ester thereof, a phytosterol ester thereof, and/or a mixture thereof.

10. The microcapsule according to claim 1, wherein the outer shell has an average diameter of from about 30 μm to about 80 μm.

11. The microcapsule according to claim 1, wherein the second polymer comprises gum arabic, casein, gellan gum, xanthan gum, pectin, alginate, or agar.

12. The microcapsule according to claim 1, wherein the second polymer comprises gum arabic or sodium caseinate.

* * * * *